(12) United States Patent
Young et al.

(10) Patent No.: US 7,740,851 B2
(45) Date of Patent: Jun. 22, 2010

(54) ULTRA HIGH AFFINITY NEUTRALIZING ANTIBODIES

(75) Inventors: James F. Young, Darnestown, MD (US); Leslie S. Johnson, Germantown, MD (US); William D. Huse, Del Mar, CA (US); Herren Wu, Houston, TX (US); Jeffry D. Watkins, Encinitis, CA (US)

(73) Assignee: MedImmune, LLC, Gaithersburg, MD (US)

( * ) Notice: Subject to any disclaimer, the term of this patent is extended or adjusted under 35 U.S.C. 154(b) by 1170 days.

(21) Appl. No.: 10/657,363

(22) Filed: Sep. 8, 2003

(65) Prior Publication Data

US 2004/0131609 A1 Jul. 8, 2004

Related U.S. Application Data

(63) Continuation of application No. 09/771,415, filed on Jan. 26, 2001, now Pat. No. 6,656,467.

(60) Provisional application No. 60/178,426, filed on Feb. 27, 2000.

(51) Int. Cl.
*A61K 39/42* (2006.01)
*A61K 39/395* (2006.01)
(52) U.S. Cl. ............... 424/147.1; 424/130.1; 424/141.1
(58) Field of Classification Search ............. 424/130–1, 424/130.1
See application file for complete search history.

(56) References Cited

U.S. PATENT DOCUMENTS

| | | | |
|---|---|---|---|
| 4,517,304 A | 5/1985 | Stott et al. |
| 4,526,938 A | 7/1985 | Churchill et al. |
| 4,659,563 A | 4/1987 | Dobkin |
| 4,717,766 A | 1/1988 | Dobkin |
| 4,760,026 A | 7/1988 | Lennox et al. |
| 4,800,078 A | 1/1989 | Prince et al. |
| 4,853,326 A | 8/1989 | Quash et al. |
| 4,917,893 A | 4/1990 | Okada et al. |
| 5,071,758 A | 12/1991 | Stott et al. |
| 5,128,326 A | 7/1992 | Balazs et al. |
| 5,137,804 A | 8/1992 | Greene et al. |
| 5,149,650 A | 9/1992 | Wertz et al. |
| 5,183,657 A | 2/1993 | Buurman |
| 5,194,595 A | 3/1993 | Wathen |
| 5,219,996 A | 6/1993 | Bodmer et al. |
| 5,223,254 A | 6/1993 | Paradiso et al. |
| 5,223,409 A | 6/1993 | Ladner et al. |
| 5,240,694 A | 8/1993 | Gwaltney, Jr. |
| 5,271,927 A | 12/1993 | Parker et al. |
| 5,279,935 A | 1/1994 | Nycz |
| 5,288,630 A | 2/1994 | Wathen |
| 5,290,540 A | 3/1994 | Prince et al. |
| 5,332,567 A | 7/1994 | Goldenberg |
| 5,332,805 A | 7/1994 | Carey et al. |
| 5,340,926 A | 8/1994 | Lowe et al. |
| 5,354,554 A | 10/1994 | Rhind |
| 5,391,478 A | 2/1995 | Greene et al. |
| 5,403,484 A | 4/1995 | Ladner et al. |
| 5,411,749 A | 5/1995 | Mayo et al. |
| 5,412,077 A | 5/1995 | Siber et al. |
| 5,418,136 A | 5/1995 | Miller et al. |
| 5,422,097 A | 6/1995 | Gwaltney, Jr. |
| 5,424,189 A | 6/1995 | Oberst et al. |
| 5,468,606 A | 11/1995 | Bogart et al. |
| 5,470,736 A | 11/1995 | Verma et al. |
| 5,476,997 A | 12/1995 | Kaneshima et al. |
| 5,484,893 A | 1/1996 | Parker et al. |
| 5,496,703 A | 3/1996 | Babish et al. |
| 5,506,209 A | 4/1996 | Mukerji et al. |
| 5,518,725 A | 5/1996 | Daynes et al. |
| 5,530,102 A | 6/1996 | Gristina et al. |
| 5,534,411 A | 7/1996 | Weltzin et al. |
| 5,538,733 A | 7/1996 | Emery et al. |
| 5,538,952 A | 7/1996 | Mukerji et al. |
| 5,571,698 A | 11/1996 | Ladner et al. |
| 5,585,089 A | 12/1996 | Queen et al. |
| 5,624,821 A | 4/1997 | Winter et al. |
| 5,648,260 A | 7/1997 | Winter et al. |
| 5,667,988 A | 9/1997 | Barbas et al. |
| 5,679,377 A | 10/1997 | Bernstein et al. |

(Continued)

FOREIGN PATENT DOCUMENTS

AU 713113 11/1999

(Continued)

OTHER PUBLICATIONS

Johnson et al., Journal of Infectious Diseases 1999, vol. 180, pp. 35-40.*

(Continued)

*Primary Examiner*—Mary E Mosher
*Assistant Examiner*—Myron G Hill
(74) *Attorney, Agent, or Firm*—Jones Day

(57) ABSTRACT

Ultra high affinity antibodies with binding affinities in the range of $10^{10}$ $M^{-1}$, and even $10^{11}$ $M^{-1}$ are disclosed. Such antibodies include antibodies having novel high affinity complementarity determining regions (CDRs), especially those with framework and constant regions derived from either humans or mice. Methods of preparing and screening such antibodies, as well as methods of using them to prevent and/or treat disease, especially virus-induced diseases, are also disclosed.

32 Claims, 10 Drawing Sheets

U.S. PATENT DOCUMENTS

| | | | |
|---|---|---|---|
| 5,693,762 A | 12/1997 | Queen et al. | |
| 5,762,905 A | 6/1998 | Burton et al. | |
| 5,811,524 A | 9/1998 | Brams et al. | |
| 5,824,307 A * | 10/1998 | Johnson | 424/133.1 |
| 5,840,298 A * | 11/1998 | Brams et al. | 424/133.1 |
| 5,855,913 A | 1/1999 | Hanes et al. | |
| 5,866,125 A | 2/1999 | Brams et al. | |
| 5,874,064 A | 2/1999 | Edwards et al. | |
| 5,912,015 A | 6/1999 | Bernstein et al. | |
| 5,916,597 A | 6/1999 | Lee et al. | |
| 5,929,212 A | 7/1999 | Jolliffe | |
| 5,934,272 A | 8/1999 | Lloyd et al. | |
| 5,939,068 A | 8/1999 | Brams et al. | |
| 5,955,364 A | 9/1999 | Brams et al. | |
| 5,958,765 A | 9/1999 | Brams et al. | |
| 5,985,309 A | 11/1999 | Edwards et al. | |
| 5,985,320 A | 11/1999 | Edwards et al. | |
| 5,989,463 A | 11/1999 | Tracy et al. | |
| 6,019,968 A | 2/2000 | Platz et al. | |
| 6,096,551 A | 8/2000 | Barbas et al. | |
| 6,117,980 A | 9/2000 | Gonzalez et al. | |
| 6,121,022 A | 9/2000 | Presta et al. | |
| 6,194,551 B1 | 2/2001 | Idusogie et al. | |
| 6,277,375 B1 | 8/2001 | Ward | |
| 6,413,771 B1 | 7/2002 | Brams et al. | |
| 6,519,948 B2 | 2/2003 | Zorn | |
| 6,528,624 B1 | 3/2003 | Idusogie | |
| 6,537,809 B2 | 3/2003 | Brams | 435/339 |
| 6,538,124 B1 | 3/2003 | Idusogie | |
| 6,565,849 B2 | 5/2003 | Koenig | |
| 6,565,888 B1 | 5/2003 | Tracy et al. | |
| 6,572,856 B1 | 6/2003 | Taylor et al. | |
| 6,656,467 B2 * | 12/2003 | Young et al. | 424/147.1 |
| 6,685,942 B1 | 2/2004 | Burton et al. | |
| 6,737,056 B1 | 5/2004 | Presta | |
| 6,818,216 B2 | 11/2004 | Young et al. | |
| 6,855,493 B2 | 2/2005 | Young et al. | |
| 7,083,784 B2 | 8/2006 | Dall'Acqua | |
| 7,132,100 B2 | 11/2006 | Oliver et al. | |
| 7,179,900 B2 | 2/2007 | Young et al. | |
| 7,208,162 B2 | 4/2007 | Prince et al. | |
| 7,229,619 B1 | 6/2007 | Young et al. | |
| 7,294,336 B2 | 11/2007 | Oliver et al. | |
| 7,323,172 B2 | 1/2008 | Young et al. | |
| 7,416,726 B2 | 8/2008 | Ravetch | |
| 7,425,618 B2 * | 9/2008 | Oliver et al. | 530/387.1 |
| 7,553,489 B2 | 6/2009 | Young et al. | |
| 2001/0026798 A1 | 10/2001 | Koenig | |
| 2001/0034062 A1 | 10/2001 | Koenig | |
| 2002/0001798 A1 | 1/2002 | Brams et al. | |
| 2002/0004046 A1 | 1/2002 | Johnson | |
| 2002/0018780 A1 | 2/2002 | Koenig | |
| 2002/0051787 A1 | 5/2002 | Prince | |
| 2002/0098189 A1 | 7/2002 | Young et al. | |
| 2002/0102257 A1 | 8/2002 | Johnson | |
| 2002/0164326 A1 * | 11/2002 | Young et al. | 424/130.1 |
| 2004/0002587 A1 | 1/2004 | Watkins | |
| 2004/0005323 A1 | 1/2004 | Brams | |
| 2004/0005324 A1 | 1/2004 | Pilkington et al. | |
| 2004/0076631 A1 | 4/2004 | Brams et al. | |
| 2004/0131609 A1 | 7/2004 | Young et al. | |
| 2005/0002926 A1 | 1/2005 | Young et al. | |
| 2006/0099220 A1 | 5/2006 | Tous et al. | |
| 2006/0115485 A1 | 6/2006 | Losonsky et al. | |
| 2006/0198840 A1 | 9/2006 | Dall'Acqua et al. | |
| 2007/0122403 A1 | 5/2007 | Dall'Acqua et al. | |
| 2007/0196916 A1 | 8/2007 | Young et al. | |
| 2008/0286270 A1 | 11/2008 | Oliver et al. | |
| 2009/0175883 A1 | 7/2009 | Oliver et al. | |

FOREIGN PATENT DOCUMENTS

| | | | |
|---|---|---|---|
| AU | 2002219944 | | 2/2008 |
| CA | 2197684 | | 10/2000 |
| EP | 0368684 | | 5/1990 |
| EP | 0413622 | | 2/1991 |
| EP | 0671927 | | 9/1995 |
| EP | 0682040 | | 11/1995 |
| EP | 0451216 | | 1/1996 |
| EP | 0699756 | | 3/1996 |
| EP | 0327378 | | 12/1996 |
| EP | 1265928 | | 12/2002 |
| FR | 2758331 | | 7/1998 |
| JP | 1268646 A | | 10/1989 |
| WO | WO 90/07861 | | 7/1990 |
| WO | WO 91/05548 | | 5/1991 |
| WO | WO 92/05274 | | 4/1992 |
| WO | WO 92/19244 | | 11/1992 |
| WO | WO 93/05796 | | 4/1993 |
| WO | WO 93/15199 | | 8/1993 |
| WO | WO 93/15200 | | 8/1993 |
| WO | WO 93/19197 | | 9/1993 |
| WO | WO 93/20210 | | 10/1993 |
| WO | WO 94/06448 | | 3/1994 |
| WO | WO 94/29351 | | 12/1994 |
| WO | WO 95/04081 | | 2/1995 |
| WO | WO 96/05229 | | 2/1996 |
| WO | WO 96/20698 | | 7/1996 |
| WO | WO 96/40252 | | 12/1996 |
| WO | WO 97/32572 | | 9/1997 |
| WO | WO 97/34631 | | 9/1997 |
| WO | WO 97/44013 | | 11/1997 |
| WO | WO 98/23289 | | 6/1998 |
| WO | WO 98/31346 | | 7/1998 |
| WO | WO 98/33919 | | 8/1998 |
| WO | WO 99/15154 | | 4/1999 |
| WO | WO 99/20253 | | 4/1999 |
| WO | WO 99/28471 | | 6/1999 |
| WO | WO 99/51642 | | 10/1999 |
| WO | WO 99/66903 | | 12/1999 |
| WO | WO 00/29584 | | 5/2000 |
| WO | WO 00/42072 | | 7/2000 |
| WO | WO 00/56771 | | 9/2000 |
| WO | WO 00/73346 | | 12/2000 |
| WO | WO 01/55217 | * | 8/2001 |
| WO | WO 01/58957 | | 8/2001 |
| WO | WO 01/64751 | | 9/2001 |
| WO | WO 01/77137 | | 10/2001 |
| WO | WO 02/060919 | | 8/2002 |
| WO | WO 03/054213 | | 7/2003 |
| WO | WO 2004/010935 | | 2/2004 |
| WO | WO 2004/016750 | | 2/2004 |
| WO | WO 2004/029207 | | 4/2004 |
| WO | WO 2004/035752 | | 4/2004 |
| WO | WO 2004/083373 | | 9/2004 |
| WO | WO 2006/34292 | | 3/2006 |
| WO | WO 2006/034292 | | 3/2006 |
| WO | WO 2007/02543 | | 1/2007 |
| WO | WO 2007/002543 | | 1/2007 |
| WO | WO 09/003019 | | 12/2008 |
| WO | WO 2009/03019 | | 12/2008 |

OTHER PUBLICATIONS

Kevin Shreder, Synthetic Haptens as Probes of Antibody Response and Immunorecognition, Methods vol. 20, Issue 3, , Mar. 2000, pp. 372-379.*

Kevin Shreder, Synthetic Haptens as Probes of Antibody Response and Immunorecognition, Methods Volume 20, Issue 3 Mar. 2000, pp. 372-379.*

Johnson et al., J of Infectious Dis. 1999 vol. 180, pp. 35-40.*

Yang et al., J. Mol. Biol. 254, 392-403 (1995).

Egan et al, Drug Res. 49 (II), 779-790 (1999).
Love et al, Biochemistry 32, 10950-10959 (1993).
Whitlow et al, Protein Engineering 8, 749-761 (1995).
Balint et al., Gene 137, 109-118 (1993).
Haynes et al. Journal of Virology. 2002; 76 (14): 6873-6881.*
Talwar et al. PNAS. 1976; 73 (1): 218-222, abstract only.*
Cruse et al. Illustrated Dictionary of Immunology. 1995. Boca Raton: CRC Press, pp. 18-19.*
Groves et al. Hybridoma. 1987; 6: 71-76.*
Dorland's Illustrated Medical Dictionary. 1994. 28th ed. Philadelphia: WB Saunders. p. 874.*
Rudikoff et al. Proc Natl Acad Sci USA. 1982; 79: 1979-1983.*
Greenspan et al. Nature Biotechnology. 1999; 7:936-937.*
Sequence alignment of SEQ ID No. 12 with Geneseq database. Accession No. AAW70933. entry date: Oct. 1998 from patent No. FR2758331-A1 of Bourgeois et al.*
Schier, et al., Isolation of Picomolar Affinity Anti-c-erbB-2 Single-chain Fv by Molecular Evolution of the Complementarity Determining Regions . . . :, Academic Press Limited, pp. 551-567 (1996).
Newman, et al., "Primatization" of Recombinant Antibodies for Immunotherapy of Human Diseases: A Macaque/Hunab Chimeric Antibody Against Human CD4, vol. 10, pp. 1455-1460, Nov. 1992.
Duenas, et al., "Selection of Phage Displayed Antibodies Based on Kinetic Constants", vol. 33, No. 3, pp. 279-285 (1996).
Duenas, et al., "In vitro Immunization of Naive Human B cells Yields High Affinity Immunoglobulin G Antibodies as Illustrated by Phage Display", pp. 1-7, Blackwell Science Ltd., (1996).
Foote, et al., "Kinetic Maturation of an Immune Response", Nature, vol. 352, (Aug. 8, 1991).
David G. Myszka, "Survey of the 1998 Optical Biosensor Literature", Journal of Molecular Recognition, (1999).
Knappik, et al., "Fully Synthetic Human Combinatorial Antibody Libraries (HuCAL) Based on Modular Consensus Frameworks and CDRs Randomized with Trinucleotides", Academic Press, pp. 57-86, (2000).
Myszka, et al., "Kinetic Analysis of a Protein Antigen-Antibody Interaction Limited by Mass Transport on an Optical Biosensor", Elsevier Science, pp. 127-137 (1997).
Johnson, et al., "Development of a Humanized Monoclonal Antibody (MEDI-493) with Potent InVitro and InVivo Activity against Respiratory Syncytial Virus," The Journal of Infectious Diseases, vol. 176, No. 5 (Nov. 1997).
Johnson, et al., "A Direct Comparison of the Activities of Two Humanized Respiratory Syncytal Virus Monoclonal Antibodies: MEDI-493 and RSHZ19," The Journal of Infectious Diseases, Vo. 180, No. 1 (Jul. 1999).
Wu, et al., "Stepwise In vitro Affinity Maturation of Vitaxin, an α,βa-specific Humanized mAb," The National Academy of Sciences, vol. 95, pp. 6037-6042 (May 1998).
Prince, et al., "Treatment of Parainfluenza Virus Type 3 Bronchiolitis and Pneumonia in a Cotton Rat Model Using Topical Antibody and Glucocorticosteroid," The Journal of Infectious Diseases, pp. 598-608 (1996).
Glaser, et al., "Antibody Engineering by Codon-Based Mutagenesis in a Filamentous Phage Vector System," The Journal of Immunology, vol. 149, pp. 3903-3913 (Dec. 1992).
Rosok, et al., "A Combinatorial Library Strategy for the Rapid Humanization of Anticarcinoma BR 96 Fab," The Journal of Biological Chemistry, vol. 271, No. 27 pp. 22611-22618 (Sep. 1995).
Karlsson, et al., "Experimental Design for Kinetic Analysis of Protein—Protein Interactions with Surface Plasmon Resonance Biosensors," The Journal of Immunological Methods, (1997).
Foote, et al., "Kinetic and Affinity Limits on Antibodies Produced During Immune Response," Proc. Nat'l. Acad. Science USA, vol. 92, pp. 1254-1256 (Feb. 1995).
Roost, et al., "Early High-Affinity Neutralizing Anti-Viral IgG Responses Without Further Overall Improvements of Affinity," Proc. Nat'l. Acad. Sci. USA, vol. 92, pp. 1257-1261 (Feb. 1995).
Everitt, et al., "The Pharmacokinetics, Antigenicity, and Fusion-Inhibition Activity of RSHZ19, a Humanized Monoclonal Antibody to Respiratory Syncytial Virus, in Healthy Volunteers," The Journal of Infectious Diseases, (1996).

Prince, et al., "Quantitative Aspects of Passive Immunity to Respiratory Syncytkal Virus Infection in Infant Cotton Rats," Journal of Virology, pp. 517-520, vol. 55, No. 3 (1985).
Raman, et al., "Diffusion-Limited Rates for Monoclonal Antibody Binding to Cytochrome," Biochemistry (1992).
Blake et al., "Automated Kinetic Exclusion Assays to Quantify Protein Binding Interactions in Homogeneous Solution," Analytical Biochemistry 272: 123-134 (1999).
Chamat et al., "Human Monoclonal Antibodies Isolated from Spontaneous Epstein-Barr Virus—Transformed Tumors of Hu-SPL-SCID Mice and Specific for Fusion Protein Display broad Neturalizing Activity Toward respiratory Syncytial Virus," The Journal of Infectious Diseases, 180:268-77 (1999).
Heard et al., "Two Neutralizing Human Anti-RSV Antibodies: Cloning, Expression, and Characterization," Molecular Medicine 5:35-45 (1999).
Wu et al., "Ultra-potent Antibodies Against Respiratory Syncytial Virus: Effects of Binding Kinetics and Binding Valence on Viral Neutralization," J. Mol. Biol. 350:126-144 (2005).
Wu et al., "Development of Motavizumab, an Ultra-potent Antibody for the Prevention of Respiratory Syncytial Virus Infection in the Upper and Lower Respiratory Tract," J. Mol. Biol. 368:652-665 (2007).
MedImmune, Inc. Annual Report (2001).
U.S. Appl. No. 09/724,396, filed Nov. 28, 2000, Young.
Abman et al., 1988, "Role of Respiratory Syncytial Virus in Early Hospitalizations for Respiratory Distress of Young Infants With Cystic Fibrosis", J Pediatr. 113(5):826-30.
Anderson et al., 1985, "Microneutralization test for respiratory syncytial virus based on an enzyme immunoassay," J. Clin. Microbiol. 22:1050-1052.
Arbiza et al., "Characterization of two antigenic sites recognized by neutralizing monoclonal antibodies directed against the fusion glycoprotein of human respiratory syncytial virus," J. Gen. Virol. 73: 2225-2234 (1992).
Barbas et al., "Selection and evolution of high-affinity human antiviral antibodies," Trends Biotech. 14(7):230-234 (1996).
Beeler et al., 1989, "Neutralization Epitopes of the F Glycoprotein of Respiratory Syncytial Virus: Effect of Mutation Upon Fusion Function", J Virol. 63(7):2941-50.
Boder et al., 2000, "Directed evolution of antibody fragments with monovalent femtomolar antigen-binding affinity," Proc. Natl. Acad. Sci. U. S. A. 97(20):10701-5.
Boeckh et al., 2001, "Phase 1 Evaluation of the Respiratory Syncytial Virus-Specific Monoclonal Antibody Palivizumab in Recipients of Hematopoietic Stem Cell Transplants." J. of Infect. Dis. 184:350-354.
Chanock et al., "Respiratory syncytial virus," Viral Infections of Humans, Epidemiology and Control, 3rd Evans, ed., A.S. Chapter 20:525-544 (1989).
Chmura et al., 2001, "Antibodies with infinite affinity." Proc. Natl. Acad. Sci. U.S.A. 98(15):8480-8484.
Chowdhury et al., 2005, "Tailor-made antibody therapeutics." Methods 36: 11-24.
Conrad et al., 1987, "Aerosolized ribavirin treatment of respiratory syncytial virus infection in infants hospitalized during an epidemic," Pediatr. Infect. Dis. J. 6(2):152-158.
Crowe et al., 1998, "Monoclonal antibody-resistant mutants selected with a respiratory syncytial virus-neutralizing human antibody fab fragment (Fab 19) define a unique epitope on the fusion (F) glycoprotein," Virology.252(2):373-5.
Dall'Acqua, 2002, "Increasing the Affinity of a Human IgG1 for the Neonatal Fc Receptor: Biological Consequences." J. of Immunol. 169: 5171-5180.
Delagrave et al., 1999, "Effects of humanization by variable domain resurfacing on the antiviral activity of a single-chain antibody against respiratory syncytial virus". Protein Eng. 12(4):357-62.
Evans et al., eds., 1989, Viral Infections of Humans: Epidemiology and Control, 3rd ed., Plenum Medical Book, New York, pp. 525-544.
Falsey et al., 1991, "Noninfluence Respiratory Virus Infection in Long-Term Care Facilities", Infect Control Hosp Epidemiol. 12(10):602-8.

Feigen et al., 1987, Textbook of Pediatric Infectious Diseases, WB Saunders, Philadelphia, pp. 1653-1675.

Fields et al., 1996, "Crystal Structure of the V-alpha domain of a T cell antigen receptor," Immunotechnology 2(4):270.

Garcia-Barreno, B. et al., "Marked Differences in the Antigenic Structure of Human Respiratory Syncytial Virus F and G Glycoproteins," J. Virology. 925-932 (1989).

Gilchrist, et al. 1994 "National surveillance for respiratory syncytial virus, United States, 1985-1990," J. Infect. Dis. 170:986-990.

Glezen et al., 1981, "Risk of Respiratory Syncytial Virus Infection for Infants From Low-Income Families in Relationship to Age, Sex, Ethnic Group, and Maternal Antibody Level", J Pediatr. 98(5):708-15.

Groothuis et al., 1988, "Respiratory Syncytial Virus Infection in Children with Bronchopulmonary Dysplasia", Pediatrics. 82(2):199-203.

Groothuis et al., 1993, "Prophylactic Administration of Respiratory Syncytial Virus Immune Globulin to High-risk Infants and Young Children", The Respiratory Syncytial Virus Immune Globulin Study Group. N Engl J Med. 329(21):1524-30.

Hacking et al., 2002, "Respiratory syncytial virus—viral biology and the host response," J. Infection 45:18-24.

Hall et al., 1975, "Nosocomial respiratory syncytial virus infections," N. Engl. J. Med. 293(26):1343-1346.

Hall et al., 1979, "Neonatal Respiratory Syncytial Virus Infection", N Engl J Med. 300(8):393-6.

Hall et al., 1983, "Aerosolized ribavirin treatment of infants with respiratory syncytial viral infection. A randomized double-blind study," N. Engl. J. Med. 308(24):1443-1447.

Hall et al., 1985, "Ribavarin treatment of respiratory syncytial viral infection in infants with underlying cardiopulmonary disease," JAMA 254(21):3047-3051.

Hall, 1987, "Respiratory syncytial virus", Textbook of Pediatric Infectious Diseases, Feigin and Cherry, eds., WB Saunders, Philadelphia, 1653-1676.

Hall, C.B., 1993, Respiratory Syncytial: What We Know Now, Contemp. Pediatrics, 10: 92-110.

Hall et al., eds., 1995, Principles and Practice of Infectious Diseases 4$^{th}$ ed., Churchill Livingstone, New York, pp. 1501-1519.

Heard et al., 1999, "Two neutralizing human RSV antibodies: cloning, expression, and characterization," Mol. Med. 5:35-45.

Hefta et al, 1998, "Kinetic and affinity constants of epitope specific anti-carcinembryonic antigen (CEA) monoclonal antibodies for CEA and engineered CEA domain constructs," Immunotechnology 4:49-57.

Hemming et al., 1985, "Studies of Passive Immunotherapy for Infections of Respiratory Syncytial Virus in the Respiratory Tract of a Primate Model", J Infect Dis. 152(5):1083-7.

Hemming et al., 1986, "Immunoglobulins in respiratory syncytial virus infections," Clinical Use of Intravenous Immunoglobulins, Morell and Nydegger., eds., Academic Press, London, pp. 285-294.

Henderson et al., 1979, "Respiratory Syncytial Virus Infections, Reinfections and Immunity. A Prospective, Longitudinal Study in Young Children", N Engl J Med. 300(10):530-4.

Hertz et al., 1989, "Respiratory Syncytial Virus-Induced Acute Lung Injury in Adult Patients With Bone Marrow Transplants: a Clinical Approach and Review of the Literature", Medicine (Baltimore). 68(5):269-81.

Kim et al., 1969, "Respiratory Syncytial Virus Disease in Infants Despite Prior Administration of Antigenic Inactivated Vaccine", Am J Epidemiol. 89(4):422-34.

Kunkel et al., 1987, "Rapid and efficient site-specific mutagenesis without phenotypic selection," Methods Enzymol. 154:367-382.

Lam et al., 1997, "Microencapsulation of Recombinant Humanized Monoclonal Antibody for Local Delivery", Proc. Int'l. Symp. Control Rel. Bioact. Mater. 24:759-760.

Lamprecht et al., 1976, "Role of Maternal Antibody in Pneumonia and Bronchiolitis Due to Respiratory Syncytial Virus", J Infect Dis. 134(3):211-7.

Landry et al., "Evaluation of reconstituted lyophilized palivizumab given intravenously at 15 and 30 mg/kg," Poster Session, Tuesday, Infect. Dis. 166A: 969.

LoBuglio et al., 1989, "Mouse/human chimeric monoclonal antibody in man: kinetics and immune response," Proc. Natl. Acad. Sci. USA 86(11):4220-4224.

MacDonald et al., 1982, "Repiratory Syncytial Viral Infection in Infants With Congenital Heart Disease", N Engl J Med. 307(7):397-400.

Malley et al., 1998, "Reduction of Respiratory Syncytial Virus (RSV) in Tracheal Aspirates in Intubated Infants by Use of Humanized Monoclonal Antibody to RSV F Protein." J. of Infect. Dis. 178:1555-1561.

Marks et al., 1992, "By-passing immunization: building high affinity human antibodies by chain shuffling," Biotechnology (N Y) 10(7):779-83.

McArthur-Vaughan et al., 2002, "A rhesus monkey model of respiratory syncytial virus infection," J. Med. Primatol. 31(2):61-73.

Medimmune, Inc. (MEDI) Release: Numax achieves primary endpoint in preliminary analysis of data from comparative phase 3 trial with Synagis (Nov. 6, 2006) BioSpace Beat, biospace.com (www.biospace.com/news_story.aspx?StoryID=36114&full=1).

Medimmune, Inc.'s (MEDI) phase I Numax study shows potential to reduce RSV disease in upper airway of children. (Sep. 1, 2005) BioSpace Beat, Biospace.com (www.biospace.com/news_story. aspx?StoryID=21014020).

Medimmune, Inc., 1999, "SYNAGIS™. package insert", revised Dec. 2, 1999.

Medimmune, SYNAGIS™, 2002, package insert, revised Oct. 23, 2002.

Meissner et al., "Safety and Pharmacokinetics of an Intramuscular Monoclonal Antibody (SB 209763) Against Respiratory Syncytial Virus (RSV) in Infants and Young Children at Risk for Severe RSV Disease", *Antimicrob Agents Chemother* 43:1183-1188 (1999).

Motavizumab vs. palivizumab for RSV infections in infants (Nov. 11, 2006) Inpharma vol. 1 No. 1563, p. 5.

Murphy et al., 1988, "Passive Transfer of Respiratory Syncytial Virus (RSV) Antiserum Suppressed The Immune Response to the RSV Fusion (F) and Large (G) Glycoproteins Expressed By Recombinant Vaccinia Viruses", J Virol. 62(10):3907-10.

Murphy et al., 1991, "Effect of Passive Antibody on the Immune Response of Cotton Rats to Purified F and G HG Glycoproteins of Respiratory Syncytial Virus (RSV)", Vaccine. 9(3):185-9.

Navas et al., 1992 , "Improved Outcome of Respiratory Syncytial Virus Infection in a High-Risk Hospitalized Population of Canadian children. Pediatric Investigators Collaborative Network on Infections in Canada", J Pediatr. 121(3):348-54.

Nguyen et al., 2000 "Efficient generation of respiratory syncytial virus (RSV)-neutralizing human MoAbs via human peripheral blood lymphocyte (hu-PBL)-SCID mice and scFv phage display libraries," Clin. Exp. Immunol. 122:85-93.

Palomo et al., "Induction of a Neutralizing Immune Response to Human Respiratory Syncytial Virus with Anti-Idiotypic Antibodies" J. Virology 64(9):4199-4206 (1990).

Physician's Desk Reference, 2001, 55$^{th}$ ed. p. 1863-1864.

Prince et al., 1983, "Mechanisms of Immunity to Respiratory Syncytial Virus in Cotton Rats", Infect Immun. 42(1):81-7.

Prince et al., 1985, "Immunoprophylaxis and Immunotherapy of Respiratory Syncytial Virus Infection in the Cotton rat", Virus Res. 3(3):193-206.

Prince et al., 1990, "Mechanism of Antibody-mediated Viral Clearance in Immunotherapy of Respiratory Syncytial Virus Infection of Cotton Rats", J Virol. 64(6):3091-2.

Prince et al., 2000, "Treatment of Respiratory Syncytial Virus Bronchiolitis and Pneumonia in a Cotton Rat Model with Systematically Administered Monoclonal Antibody (Palivizumab) and Glucocorticosteroid," J Inf Diseases 182:1326-1330.

Prince (2001) "An update of respiratory syncytial virus antiviral agents." Expert Opin Investig Drugs. 10(2):297-308.

Prince, 1975, "The Pathogenesis of Respiratory Syncytial Virus Infection in Infant Ferrets" Ph.D. Dissertation, University of California-Los Angeles.

Roguska et al., "Humanization of murine monoclonal antibodies through variable domain resurfacing," Proc. Natl. Acad. Sci. U.S.A. 91(3):969-973 (1994).

Saez-Llorens et al., 1997, "Phase I/II open label multi dose escalation trial of a humanized respiratory syncytial virus (RSV) monoclonal antibody (Medi-493) administered intramuscularly (IM) in high risk children," Abstract in Non HIV virology, ICAAC Toronto.

Saez-Llorens et al., 1998, "Safety and Pharmacokinetics of an Intramuscular Humanized Monoclonal Antibody to Respiratory Syncytial Virus in Premature infants, and infants with Bronchopulmonary Dysplasia", The MEDI-493 Study Group, Pediatric Infect Dis J. 17(9):787-91.

Sahagan et al., 1986, "A genetically engineered murine/human chimeric antibody retains specificity for human tumor-associated antigen," J. Immunol. 137(3):1066-1074.

Sakurai et al., 1999, "Human antibody responses to mature and immature forms of viral envelope in respiratory syncytial virus infection: significance for submit vaccines." J. Virol. 73(4):2956-2962.

Schier et al.,. 1996, "Isolation of high-affinity monomeric human anti-c-erbB-2 single chain Fv using affinity-driven selection." J Mol Biol. 255(1):28-43.

Smith et al., 1991, "A Controlled Trial of Aerosolized Ribavirin in Infants Receiving Mechanical Ventilation for Severe Respiratory Syncytial Virus Infection", N Engl J Med. 325(1):24-9.

Sorbera et al., 1998, "Palivizumab," Drugs Data Report 20:702-703.

Sorbera et al., 1998, "Palivizumab," Drugs of the Future 23:970-976.

Steplewski et al., 1988, "Biological activity of human-mouse IgG1, IgG2, IgG3, and IgG4 chimeric monoclonal antibodies with antitumor specificty," Proc. Natl. Acad. Sci. USA 85(13):4852-4856.

Subramanian et al., "Safety, Tolerance and Pharmacokinetics of a Humanized Monoclonal Antibody to Respiratory Syncytial Virus in Premature Infants and Infants with Bronchopulmonary Dysplasia", Pediatric Infect Dis J. 17:110-115.

Subramanian et al., 1997, "Randomized double blind placebo controlled dose escalation trial of a humanized repiratory syncytial virus monoclonal antibody in high risk infants," Poster session infect. dis. 130A:768.

Sun et al., 1987, "Chimeric antibody with human constant regions and mouse variable regions directed against carcinoma-associated antigen 17-1A," Proc. Natl. Acad. Sci. USA 84(1):214-218.

Takeda et al., 1985, "Construction of chimaeric processed immunoglobulin genes containing mouse variable and human constant region sequences," Nature 314(6010):452-454.

The Impact-RSV Study Group, "Palivizumab, a humanized respiratory syncytial virus monoclonal antibody, reduces hospitalization from respiratory syncytial virus infection in high-risk infants." Pediatrics. Sep. 1998; 102(3 Pt 1):531-537.

Thompson et al., 1996, "Affinity maturation of a high-affinity human monoclonal antibody against the third hypervariable loop of human immunodeficiency virus: use of phage display to improve affinity and broaden strain reactivity," J. Mol. Biol. 256(1):77-88.

Van Der Merwe et al., 1993, "Affinity and kinetic analysis of the interaction of the cell adhesion molecules rat CD2 and CD48," EMBO J. 12(13):4945-4954.

Van Der Merwe et al., 1994, "Human cell-adhesion molecule CD2 binds CD58 (LFA-3) with a very low affinity and an extremely fast dissociation rate but does not bind CD48 or CD59," Biochemistry 33(33):10149-10160.

Vancott et al., 1994, "Dissociation rate of antibody-gp120 binding interactions is predictive of V3-mediated neutralization of HIV-1," J. Immunol. 153(1):449-59.

Walsh et al., 1987, "Immunization with Glycoprotein Subunits of Respiratory Syncytial Virus to Protect Cotton Rats Against Viral Infection", J Infect Dis. 155(6):1198-204.

Weltzin et al., 1994, "Intranasal Monoclonal Immunoglobulin A against Respiratory Syncytial Virus Protects against Upper and Lower Respiratory Tract Infections in Mice." Anitmicro Agents & Chemo. 38(12):2785-2791.

Weltzin et al., 1996, "Intranasal Monoclonal IgA Antibody to Respiratory Syncytial Virus Protects Rhesus Monkeys against Upper and Lower Tract Infection." J. of Infect Dis. 174:256-241.

Wu et al, 2002, "Tailoring Kinetics of Antibodies Using Focused Combinatorial Libraries" chapter 13 from Methods in Molecular Biology vol. 207, Eds. Welschop and Krauss, Humana Press Inc., Totowa, NJ, pp. 213-233.

Wu et al., 1998, "Stepwise in vitro affinity maturation of Vitaxin, an avb-specific humanized mAb," PNAS 95:6037-6042.

Wu et al., 1999, "Humanization of murine monoclonal antibody by simultaneous optimization of framework and CDR residues," J. Mol. Biol. 294(1): 151-62.

U.S. Appl. No. 09/724,396—Office Action dated Mar. 26, 2002.
U.S. Appl. No. 09/724,396—Office Action dated Dec. 3, 2002.
U.S. Appl. No. 09/724,396—Office Action dated Jun. 3, 2003.
U.S. Appl. No. 09/724,396—Office Action dated Jul. 28, 2003.
U.S. Appl. No. 09/724,396—Office Action dated Apr. 5, 2004.
U.S. Appl. No. 09/724,531 (U.S. Patent No. 7,229,619)—Office Action dated Feb. 21, 2003.
U.S. Appl. No. 09/724,531 (U.S. Patent No. 7,229,619)—Office Action dated Oct. 21, 2003.
U.S. Appl. No. 09/724,531 (U.S. Patent No. 7,229,619)—Office Action dated Jun. 4, 2004.
U.S. Appl. No. 09/724,531 (U.S. Patent No. 7,229,619)—Office Action dated Feb. 9, 2005.
U.S. Appl. No. 09/724,531 (U.S. Patent No. 7,229,619)—Office Action dated Jun. 15, 2005.
U.S. Appl. No. 09/724,531 (U.S. Patent No. 7,229,619)—Office Action dated Apr. 4, 2006.
U.S. Appl. No. 09/724,531 (U.S. Patent No. 7,229,619)—Office Action dated Aug. 22, 2006.
U.S. Appl. No. 09/724,531 (U.S. Patent No. 7,229,619)—Office Action dated Jan. 30, 2007.
U.S. Appl. No. 09/996,288 (U.S. Patent No. 6,818,216)—Office Action dated Jul. 14, 2003.
U.S. Appl. No. 09/996,288 (U.S. Patent No. 6,818,216)—Office Action dated Jan. 29, 2004.
U.S. Appl. No. 09/996,288 (U.S. Patent No. 6,818,216)—Office Action dated Jun. 30, 2004.
U.S. Appl. No. 09/996,265 (U.S. Patent No. 6,855,493)—Office Action dated Aug. 12, 2003.
U.S. Appl. No. 09/996,265 (U.S. Patent No. 6,855,493)—Office Action dated Mar. 31, 2004.
U.S. Appl. No. 09/996,265 (U.S. Patent No. 6,855,493)—Office Action dated Jul. 13, 2004.
U.S. Appl. No. 10/403,180 (U.S. Patent No. 7,179,900)—Office Action dated Apr. 4, 2005.
U.S. Appl. No. 10/403,180 (U.S. Patent No. 7,179,900)—Office Action dated Oct. 19, 2005.
U.S. Appl. No. 10/403,180 (U.S. Patent No. 7,179,900)—Office Action dated Mar. 30, 2006.
U.S. Appl. No. 10/403,180 (U.S. Patent No. 7,179,900)—Office Action dated Sep. 6, 2006.
U.S. Appl. No. 10/900,230 (U.S. Publ. No. 2005/0002926)—Office Action dated Jan. 24, 2006.
U.S. Appl. No. 10/900,230 (U.S. Publ. No. 2005/0002926)—Office Action dated Jun. 30, 2006.
U.S. Appl. No. 10/900,230 (U.S. Publ. No. 2005/0002926)—Office Action dated Dec. 26, 2006.
U.S. Appl. No. 10/900,230 (U.S. Publ. No. 2005/0002926)—Office Action dated Jun. 27, 2007.
U.S. Appl. No. 10/900,230 (U.S. Publ. No. 2005/0002926)—Office Action dated Feb. 21, 2008.
U.S. Appl. No. 10/962,285 (U.S. Patent No. 7,323,172)—Office Action dated Oct. 26, 2006.
U.S. Appl. No. 10/962,285 (U.S. Patent No. 7,323,172)—Office Action dated Apr. 13, 2007.
U.S. Appl. No. 09/796,848 (U.S. Publ. No. 2002/0098189)—Office Action dated Jun. 18, 2002.
U.S. Appl. No. 09/796,848 (U.S. Publ. No. 2002/0098189)—Office Action dated Dec. 29, 2003.
U.S. Appl. No. 09/796,848 (U.S. Publ. No. 2002/0098189)—Office Action dated Oct. 29, 2004.
U.S. Appl. No. 09/796,848 (U.S. Publ. No. 2002/0098189)—Office Action dated Jul. 13, 2005.
U.S. Appl. No. 09/796,848 (U.S. Publ. No. 2002/0098189)—Office Action dated Apr. 4, 2006.
U.S. Appl. No. 09/796,848 (U.S. Publ. No. 2002/0098189)—Office Action dated Jul. 27, 2007.

U.S. Appl. No. 09/796,848 (U.S. Publ. No. 2002/0098189)—Office Action dated Apr. 14, 2008.
U.S. Appl. No. 11/263,230 (U.S. Publ. No. 2006/0115485)—Office Action dated Jan. 9, 2008.
U.S. Appl. No. 11/643,982 (U.S. Publ. No. 2007/0196916)—Office Action dated Sep. 2, 2008.
U.S. Appl. No. 10/900,230 (U.S. Publ. No. 2005/0002926)—Office Action dated Sep. 18, 2008.
U.S. Appl. No. 10/962,285 (U.S. Patent No. 7,323,172)—Office Action / Notice of Allowability dated Sep. 6, 2007.
U.S. Appl. No. 11/263,230 (U.S. Publ. No. 2006/0115485)—Office Action dated Oct. 2, 2008.
U.S. Appl. No. 09/771,415 (U.S. Patent No. 6,656,467)—Office Action dated Jun. 18, 2002.
U.S. Appl. No. 09/771,415 (U.S. Patent No. 6,656,467)—Office Action dated Feb. 10, 2003.
U.S. Appl. No. 09/771,415 (U.S. Patent No. 6,656,467)—Office Action / Notice of Allowability dated May 6, 2003.
U.S. Appl. No. 10/020,354 (U.S. Patent No. 7,083,784)—Office Action dated Apr. 7, 2004.
U.S. Appl. No. 10/020,354 (U.S. Patent No. 7,083,784)—Office Action dated Nov. 17, 2004.
U.S. Appl. No. 10/020,354 (U.S. Patent No. 7,083,784)—Office Action dated Jun. 1, 2005.
U.S. Appl. No. 10/020,354 (U.S. Patent No. 7,083,784)—Office Action / Notice of Allowability dated Dec. 15, 2005.
Dall'Acqua Declatation (dated Oct. 3, 2005)—Filed in U.S. Appl. No. 10/202,354 (U.S. Patent No. 7,083,784) on Oct. 8, 2005.
U.S. Appl. No. 11/397,328 (U.S. Publ. No. 2006/0198840)—Office Action dated Oct. 18, 2007.
U.S. Appl. No. 11/397,328 (U.S. Publ. No. 2006/0198840)—Office Action / Notice of Allowability dated Aug. 7, 2008.
U.S. Appl. No. 10/461,904 (U.S. Patent No. 7,132,100)—Office Action dated Dec. 14, 2004.
U.S. Appl. No. 10/461,904 (U.S. Patent No. 7,132,100)—Office Action dated Nov. 25, 2005.
U.S. Appl. No. 10/461,904 (U.S. Patent No. 7,132,100)—Office Action / Notice of Allowability dated May 2, 2006.
U.S. Appl. No. 11/362,267 (U.S. Patent No. 7,294,336)—Office Action dated May 4, 2007.
U.S. Appl. No. 11/362,267 (U.S. Patent No. 7,294,336)—Office Action / Notice of Allowability dated Aug. 6, 2007.
U.S. Appl. No. 10/461,863 (U.S. Patent No. 7,425,618)—Office Action dated Dec. 18, 2006.
U.S. Appl. No. 10/461,863 (U.S. Patent No. 7,425,618)—Office Action dated Jun. 11, 2007.
U.S. Appl. No. 10/461,863 (U.S. Patent No. 7,425,618)—Office Action / Notice of Allowability dated Nov. 19, 2007.
Adams et al., 1998. Increased affinity leads to improved selective tumor delivery of single-chain Fv antibodies, Cancer Res. 58(3):485-90.
American Academy of Pediatrics Committee on Infectious Diseases: Use of Ribavirin in the Treatment of Respiratory Syncytial Virus Infection. Pediatrics. Sep. 1993;92(3):501-4.
Bennett et al., 2007. Immunopathogenesis of Respiratory Syncytial Virus Bronchiolitis, JID, 195:1532-1540.
Bentley and Rabbits, 1980. Human immunoglobulin variable region genes— DNA Sequences of Two V Kappa Genes and a Pseudogene, Nature 288: 730-733.
Boulianne et al., 1984. Production of functional chimaeric mouse/human antibody, Nature 312(5995):643-646.
Carson and Freimark, 1986. Human lymphocyte hybridomas and monoclonal antibodies, Adv. Immunol. 38:275-311.
Chothia et al., 1998. Structural determinants in the sequences of immunoglobulin variable domain. J Mol Biol. 278(2):457-79.
Cleek et al., 1997. Biodegradable Polymeric Carriers for a bFGF Antibody for Cardiovascular Application, Pro. Int'l Symp. Control. Rel Bioact. Mater. 24: 853-854.
Colman, 1994. Effects of amino acid sequence changes on antibody-antigen interactions; Res Immunol. 145(1):33-6.

Crowe et al., 1994. Recombinant human respiratory syncytial virus (RSV) monoclonal antibody Fab is effective therapeutically when introduced directly into the lungs of RSV-infected mice, Proc. Natl. Acad. Sci. USA, 91:1386-1390.
DeVincenzo, 2005. Factors Predicting Childhood Respiratory Syncytial Virus Severity. What They Indicate About Pathogenesis. The Pediatric Infectious Disease Journal, 24(11):S177-S183.
Downham et al., 1976. Breast-feeding protects against respiratory syncytial virus infections. Br Med J. 2(6030):274-6.
Edelman et al., 1969. The Covalent Structure of an Entire gammaG Immunoglobulin Molecule. PNAS 63:78-85.
Fields et al., 1990, Fields Virology, 2nd Ed., vol. 1, Raven Press, NY p. 1045-1072.
Garvie and Gray, 1980. Outbreak of Respiratory Syncytial Virus Infection in the Elderly, Br Med J. 281(6250):1253-4.
Gillies et al., 1989. High-level expression of chimeric antibodies using adapted cDNA variable region cassettes. J. Immunol Methods. 125:191-202.
Hemming et al., 1988. Topically Administered Immunoglobulin Reduces Pulmonary Respiratory Syncytial Virus Shedding in Owl Monkeys, Antimicrobial Agents and Chemotherapy, 32(8):1269-1270.
Howard et al., 1989. Intracerebral Drug Delivery in Rats with Lesion-Induced Memory Deficits, J Neurosurg. 71(1):105-12.
Hudson and Souriau, 2003. Engineered Antibodies. Nature Medicine 9(1):129-34.
Ichiyoshi et al., 1995. A human anti-insulin IgG autoantibody apparently arises through clonal selection from an insulin-specific "germline" natural antibody template. Analysis by V gene segment reassortment and site-directed mutagenesis, J. Immunol. 154(1):226-38.
Jackson et al 1998. Antigen specificity and tumour targeting efficiency of a human carcinoembryonic antigen-specific scFv and affinity-matured derivatives, Br. J. Cancer 78(2):181-8.
Johnson et al., 1987. The G Glycoprotein of Human Respiratory Syncytial Viruses of Subgroups A and B: Extensive Sequence Divergence Between Antigenically Related Proteins, Proc Natl Acad Sci U S A.
Johnson et al., 1991. Development of humanized monoclonal antibodies which neutralize respiratory syncytial virus. J. Cellular Biochem. Suppl. 15E. P.120, Abstract No. 108.
Kapikian et al., 1969. An Epidemiologic Study of Altered Clinical Reactivity to Respiratory Syncytial (RS) Virus Infection in Children Previously Vaccinated With an Inactivated RS Virus Vaccine, Am J Epidemiol. 89(4):405-21.
Levy et al., 1985. Inhibition of Calcification of Bioprosthetic Heart Valves by Local Controlled-release Diphosphonate, Science. 228(4696):190-2.
Liu et al., 1987. Expression of mouse::human immunoglobulin heavy-chain cDNA in lymphoid cells, Gene 54(1):33-40.
Maynard et al., 2002. Protection against anthrax toxin by recombinant antibody fragments correlates with antigen affinity, Nat. Biotechnol. 20(6):597-601.
Mejias et al., 2005. Respiratory syncytial virus infections: Old challenges and new opportunities, Ped. Infect. Dis. J. 24: S189-S197.
Mejias et al., 2005. Comparative Effects of Two Neutralizing Anti-Respiratory Syncytial Virus (RSV) Monoclonal Antibodies in the RSV Murine Model: Time versus Potency, Antimicrobial Agents and Chemotherapy vol. 49, No. 11: 4700-4707.
Morrison et al., 1984. Chimeric human antibody molecules: mouse antigen-binding domains with human constant region domains, Proc. Natl. Acad. Sci. USA 81(21):6851-6855.
Morrison et al., 1985. Transfectomas provide novel chimeric antibodies, Science 229(4719):1202-1207.
Murphy et al., 1994. An Update on Approaches to the Development of Respiratory Syncytial Virus (RSV) and Paraintluenza Virus Type 3 (PIV3) Vaccines, Virus Res. 32(1):13-36.
Ning et al., 1996. Intratumoral Radioimmunotherapy of a Human Colon Cancer Xenograft Using a Sustained Release Gel, Radiotherapy and Oncology 39: 179-89.
Ogra et al., 1988. Respiratory Syncytial Virus Infection and the Immunocompromised Host, Pediatr Infect Dis J. Apr. 1988;7(4):246-9.

Orkin and Motulsky, Report and recommendations of the panel to assess the NIH investment in research on gene therapy, available from http://www.nih.gov/news/panelrep.html (1995).

Padlan, 1991. A possible procedure for reducing the immunogenicity of antibody variable domains while preserving their ligand-binding properties. Mol. Immunol. 28(4/5):489-498.

Pohl et al., 1992. Respiratory Syncytial Virus Infections in Pediatric Liver Transplant Recipients, J Infect Dis. 165(1):166-9.

Press et al., 1970. The Amino Acid Sequences of the Fd Fragments of Two Human Gamma-1 Heavy chains, Biochem J. I 17(4):641-60.

Prince et al., 1987. Effectiveness of Topically Administered Neutralizing Antibodies in Experimental Immunotherapy of Respiratory Syncytial Virus Infection in Cotton Rats, Journal of Virology, 61(6);1851-1854.

Riechmann et al., 1988. Reshaping human antibodies for therapy. Nature. 332(6162):323-7.

Ruuskanen et al., 1993. Respiratory syncytial virus, Curr Probl Pediatr. 23(2):50-79.

Saudek et al., 1989. A Preliminary Trial of the Programmable Implantable Medication System for Insulin Delivery. N. Engl J Med. 321(9):574-9.

Scott et al., 1985. Cellular reactivity to respiratory syncytial virus in human colostrum and breast milk. J Med Virol. 17(1):83-93.

Sefton, 1987. Implantable Pumps, CRC Crit. Rev. Biomed. Eng. 14:201-240.

Sevier et al., 1981. Monoclonal antibodies in clinical immunology. Clin Chem. 27(11):1797-806.

Song et al., 1995. Antibody Mediated Lung Targeting of Long-Circulating Emulsions, PDA Journal of Pharmaceutical Science & Technology 50: 372-77.

Studnicka et al., 1994. Human-engineered monoclonal antibodies retain full specific binding activity by preserving non-CDR complementarity-modulating residues. Protein Eng. 7:805-814.

Taylor et al., 1984. Monoclonal antibodies protect against respiratory syncytial virus infection in mice. Immunology. 52(1):137-42.

Taylor et al., 1992. Protective epitopes on the fusion protein of respiratory syncytial virus recognized by murine and bovine monoclonal antibodies. J Gen Virol. 73 ( Pt 9):2217-23.

Van Wyke Coelingh et al., 1985. Antigenic variation in the hemagglutinin-neuraminidase protein of human parainfluenza type 3 virus, Virology 143(2):569-582.

Verma et al., 1997. Gene therapy - promises, problems and prospects, Nature 389:239-242.

Wald et al., 1988. In re ribavirin: a case of premature adjudication? J. Pediatr. 112(1):154-158.

Walsh et al., 1984. Protection from respiratory syncytial virus infection in cotton rats by passive transfer of monoclonal antibodies. Infect Immun. 43(2):756-8.

Watkins et al., 1997. Determination of the relative affinities of antibody fragments expressed in Escherichia coli by enzyme-linked immunosorbent assay. Anal Biochem. 253(1):37-45.

Wright et al., 1982. Administration of a highly attenuated, live respiratory syncytial virus vaccine to adults and children, Infect. Immun. 37(1):397-400.

Wu et al., 2008. Immunoprophylaxis of RSV Infection: Advancing from RSV-IGIV to Palivizumab and Motavizumab in Human Antibody Therapeutics for Viral Disease. Current Topics in Microbiology and Immunology 317. Springer-Verlag Berlin Heidelberg, p. 103-123.

U.S. Appl. No. 10/900,230 (U.S. Publ. No. 2005/0002926) - Interview Summary dated Mar. 27, 2009.

U.S. Appl. No. 09/796,848 (U.S. Publ. No. 2002/0098189) - Office Action dated Jan. 22, 2009.

U.S. Appl. No. 12/075,197, filed Mar. 10, 2008, Oliver et al.

Abbas et al., 1991. Cellular and Molecular Immunology- Chapter 3- Antibodies and Antigens, p. 45-47; W.B Saunders Company.

Ames et al., 1995. Conversion of murine Fabs isolated from a combinatorial phage display library to full length immunoglobulins. J. Immunol Methods.184(2):177-86.

Berzofsky and Berkower, 1993. In Paul, W.E., Fundamental Immunology (Raven Press), Chapter 8: Immunogenicity and antigen structure. p. 242.

Berzofsky and Berkower, 1993. In Paul, W.E., Fundamental Immunology (Raven Press), Chapter 9: Structure and Function of Immunoglobulins, p. 292-295.

Better et al., 1988. Escherichia coli secretion of an active chimeric antibody fragment. Science. 240(4855):1041-3.

Brinkmann et al., 1995. Phage display of disulfide-stabilized Fv fragments. J Immunol Methods. 182(1):4150.

Burton and Barbas, 1994. Human antibodies from combinatorial libraries. Adv. Immunol. 57:191-280.

Cao et al., 2003. Bispecific antibody conjugates in therapeutics; Adv Drug Deliv Rev. 55(2):171-97.

Casset et al., 2003. A peptide mimetic of an anti-CD4 monoclonal antibody by rational design. Biochem Biophys Res Commun. 307(1):198-205.

Connors, 1990. Chemical Kinetics: The Study of Reaction Rates in Solution, p. 152.

Fahy and O'Byrne, 2001. Reactive Airways Disease. Am J Respir Crit Care Med. 163(4):822-3.

Foecking and Hofstetter, 1986. Powerful and versatile enhancer-promoter unit for mammalian expression vectors. Gene. 45:101-105.

Hammerling et al., 1981. Production of Antibody-Producing Hybridomas in the Rodent Systems, in Monoclonal antibodies and T-cell hybridomas, Elsevier, NY. p. 563-587.

Hellstrom et al., 1987. Antibodies for drug delivery, in Controlled Drug Delivery, Fundamentals and Applications 2nd edition. Chapter 15: p. 623-653.

Kettleborough et al., 1994. Isolation of tumor cell-specific single-chain Fv from immunized mice using phage-antibody libraries and the re-construction of whole antibodies from these antibody fragments. Eur J Immunol. 24(4):952-8.

Langer and Peppas, 1983. Chemical and physical structure of polymers as carriers for controlled release of bioactive agents: A review. J Macromol. Sci.- Rev. Macromol. Chem. Phys.C23(1):61-126.

Langer, 1990. New methods of drug delivery. Science. 249:1527-1533.

Lee et al., 1998. Demonstration of IgM antibodies of high affinity within the anti-Galalphal-3Gal antibody repertoire. Transplantation; 66(8):1117-9.

Lonberg and Huszar, 1995. Human antibodies from transgenic mice. Int. Rev. Immunol. 13:65-96.

Mullinax et al., 1992. Expression of a heterodimeric Fab antibody protein in one cloning step. Bio Techniques. 12:864-869.

O'Byrne and Postma, 1999. The Many Faces of Airway Inflammation. Am J Respir Crit Care Med. May 1999;159(5 Pt 2):S41-63.

Persic et al., 1997. An integrated vector system for the eukaryotic expression of antibodies or their fragments after selection from phage display libraries. Gene. 187(1):9-18.

Ruther and Muller-Hill, 1983. Easy identification of cDNA clones. EMBO J. 2:1791-1794.

Takahashi et al. 1984. Rearranged immunoglobulin heavy chain variable region (VH) pseudogene that deletes the second complementarity-determining region. PNAS 81: 5194-198.

Weltzin et al., 1989. Binding and transepithelial transport of immunoglobulins by intestinal M cells: demonstration using monoclonal IgA antibodies against enteric viral proteins. J. Cell Biol. 108(5):1673-85.

Weltzin et al., 1999, Intranasal antibody prophylaxis for protection against viral disease. Clin Microbiol Rev. 12(3):383-93.

Wilson et al., 1984. The structure of an antigenic determinant in a protein. Cell. 37(3):767-78.

Adams et al, 1998. Prolonged in vivo tumor retention of a human diabody targeting the extracellular domain of human HER2/neu, Br J Cancer; 77(9): 1405-12.

Bennett et al., 2007, Immunopathogenesis of Respiratory Syncytial Virus Bronchiolitis, J Infect Dis; 195(10):1532-1540.

Carlsson et al., 1992. Human peripheral blood lymphocytes transplanted into SCID mice constitute an in vivo culture system exhibiting several parameters found in a normal humoral immune response and are a source of immunocytes for the production of human monoclonal antibodies. J Immunol. 1992; 148(4):1065-71.

Crowe et al., 1993, Recombinant human respiratory syncytial virus (RSV) monoclonal antibody Fab is effective therapeutically when introduced directly into the lungs of RSV-infected mice, Proc Natl Acad Sci USA; 91:1386-1390.

De Vincenzo et al., 2005, Factors Predicting Childhood RespiratorySyncytial Virus Severity - What They Indicate About Pathogenesis, Ped Inf Dis; 24:S177-S183.

Ifverson and Borrebaeck, 1996. SCID-hu-PBL: A model for making human antibodies? Semin Immunol. 8(4):243-8.

Hemming et al., 1988, Topically Administered Immunoglobulin Reduces PulmonaryRespiratory Syncytial Virus Shedding in Owl Monkeys, Antimicrob Agents Chemother; 32(8):1269-1270.

Krishnan et al., 2008, Therapeutic addition of motavizumab, a monoclonal antibody against respiratory syncytial virus (RSV), modulates epithelial cell responses to RSV infection., Annual Interscience Conf Antimicrobial Agents Chemotherapy/Annual Meed Infect Dis Soc Am; 48/46 Oct. 28 Abstract V-4147.

Kudo et al., 1992. New strategies to establish human monoclonal antibodies; Tohoku J Exp Med. 168(2):323-327.

Kudo et al., 1993. Production of a human monoclonal antibody to a synthetic peptide by active in vivo immunization using a SCID mouse grafted with human lymphocytes; Tohoku J Exp Med. 171:327-338.

Lagos et al., 2005, Administration of the anti-RSV monoclonal antibody (Mab) Numax™ is associated with a reduction in upper airway (UA) RSV load, World Congress Pediatr Infect Disease; Sep. 1-4.

Maccallum et al., 1996. Antibody-antigen interactions: contact analysis and binding site topography. J Mol Biol. 262(5):732-45.

McCall et al., 1999. Isolation and characterization of an anti-CD 16 single-chain Fv fragment and construction of an anti-HER2/neu/anti-CD16 bispecific scFv that triggers CD16-dependent tumor cytolysis. Mol Immunol. May 1999;36(7):433-45.

Prince et al., 1987, Effectiveness of Topically Administered Neutralizing Antibodies inExperimental Immunotherapy of Respiratory Syncytial Virus Infection in Cotton Rats, J Virol; 61(6):1851-1854.

Richter et al., 2008, Respiratory syncytial virus (RSV) therapy utilizing intranasally delivered motavizumab, a monoclonal antibody against F protein, Annual Interscience Conf Antimicrobial Agents Chemotherapy/Annual Meed Infect Dis Soc Am; 48/46 Oct. 28 Abstract V-4145.

Seaver, 1994. Monoclonal antibodies in industry: More difficult than originally thought; Genetic Engineering News, vol. 14, No. 14, p. 10 and 21.

Stott et al., 1984. The characterization and uses of monoclonal antibodies to respiratory syncytial virus. Dev Biol Stand. 57:237-44.

Ware et al., 1985. Human, rat or mouse hybridomas secrete high levels of monoclonal antibodies following transplantation into mice with severe combined immunodeficiency disease (SCID). J Immunol Methods. 85(2):353-61.

Watkins et at., 1998. Discovery of human antibodies to cell surface antigens by capture lift screening of phage-expressed antibody libraries. Anal Biochem. 256(2):169-77.

Wu et al., 2008, Immunoprophylaxis of RSV Infection: Advancing from RSV-IGIV to Palivizumab and Motavizumab, Curr Topics Microbiol Immunol; 317:103-123.

International Search Report for WO 01/555217 dated Jun. 6, 2001.

International Preliminary Examination Report for WO 01/555217 (including Annex) dated Apr. 10, 2002.

EP Serial No. 01903352 (EP 1265928) - Examination Report dated May 12, 2006.

EP Serial No. 01903352 (EP 1265928) - Response to Examination Report dated Nov. 17, 2006.

EP Serial No. 01903352 (EP 1265928) - Examination Report dated Sep. 25, 2007.

EP Serial No. 01903352 (EP 1265928) - Response to Examination Report dated Apr. 7, 2008.

EP Serial No. 01903352 (EP 1265928) - Summons to Oral Proceedings and Preliminary Opinion dated Apr. 3, 2009.

U.S. Appl. No. 12/476,183, filed Jun. 1, 2009, Young et al.

U.S. Appl. No. 12/559,375, filed Sep. 14, 2009, Young et al.

EP Serial No. 01903352 (EP 1265928) - Response to Examination Report dated Jul. 10. 2009.

EP Serial No. 01903352 (EP 1265928) - Interview Summary dated Aug. 3, 2009.

EP Serial No. 01903352 (EP 1265928) - Examination Report dated Aug. 10, 2009.

EP Serial No. 01903352 (EP 1265928) - Response to Examination Report dated Oct. 20, 2009.

U.S. Appl. No. 10/900,230 (U.S. Publ. No. 2005/0002926) - Office Action / Notice of Allowability dated Jun. 17, 2009.

U.S. Appl. No. 11/643,982 (U.S. Publ. No. 2007/0196916) - Office Action / Notice of Allowability dated Feb. 13, 2009.

U.S. Appl. No. 11/263,230 (U.S. Publ. No. 2006/0115485) - Office Action dated Mar. 30, 2009.

U.S. Appl. No. 11/397,328 (U.S. Publ. No. 2006/0198840) - Office Action dated Feb. 13, 2009.

U.S. Appl. No. 11/397,328 (U.S. Publ. No. 2006/0198840) - Office Action / Notice of Allowability dated Sep. 29, 2009.

U.S. Appl. No. 11/649,455 ( U.S. Publ. No. 2007/0122403) - Office Action dated Feb. 26, 2009.

U.S. Appl. No. 11/906,543 (U.S. Publ. No. 2008/0286270) - Office Action dated Jun. 12, 2009.

U.S. Appl. No. 11/906,543 (U.S. Publ. No. 2008/0286270) - Office Action dated Oct. 19, 2009.

* cited by examiner

DIQMTQSPST LSASVGDRVT ITC <u>SASSSVGYMH</u> WYQQKPG    40
                              CDR L1

KAPKLLIY <u>DTSKLAS</u> GVPSR FSGSGSGTEF TLTISSLQPD    80
           CDR L2

DFATYYC <u>FQGSGYPFT</u> FGGGTKVEIK                    106
           CDR L3

B

QVTLRESGPA LVKPTQTLTL TCTFSGFSLS <u>TSGMSVG</u> WIR     40
                                    CDR H1

QPPGKALEWL A <u>DIWWDDKKDYNPSLKS</u> RLT ISKDTSKNQV     80
                 CDR H2

VLKVTNMDPA DTATYYCAR <u>SMITNWYFDV</u> W GQGTTVTVSS    120
                        CDR H3

DIQMTQSPST LSASVGDRVT ITC <u>SASSSVGYMH</u> WYQQKPG     40
                                                   CDR L1

KAPKLLIY   <u>DTSKLAS</u>   GVPSR   FSGSGSGTEF  TLTISSLQPD     80
             CDR L2

DFATYYC   <u>FQGSFYPFT</u>   FGGGTKVEIK     106
             CDR L3

B

QVTLRESGPA LVKPTQTLTL TCTFSGFSLS  <u>TAGMSVG</u>  WIR     40
                                                                   CDR H1

QPPGKALEWL A <u>DIWWDDKKDYNPSLKS</u> RLT ISKDTSKNQV     80
                             CDR H2

VLKVTNMDPA DTATYYCAR <u>SMITNFYFDV</u> W GQGTTVTVSS     120
                                   CDR H3

DIQMTQSPST LSASVGDRVT ITC <u>SASSSVGYMH</u> WYQQKPG   40
                                        CDR L1

KAPKLLIY <u>DTFKLAS</u> GVPSR FSGSGSGTEF TLTISSLQPD   80
          CDR L2

DFATYYC <u>FQGSGYPFT</u> FGGGTKVEIK   106
         CDR L3

B

QVTLRESGPA LVKPTQTLTL TCTFSGFSLS <u>TAGMSVG</u> WIR   40
                                            CDR H1

QPPGKALEWL A <u>DIWWDDKKDYNPSLKS</u> RLT ISKDTSKNQV   80
               CDR H2

VLKVTNMDPA DTATYYCAR <u>SMITNFYFDV</u> W GQGTTVTVSS   120
                              CDR H3

DIQMTQSPST LSASVGDRVT ITC SASSSVGYMH WYQQKPG     40
                                          CDR L1

KAPKLLIY   DTFKLAS   GVPSR   FSGSGSGTEF TLTISSLQPD     80
                CDR L2

DFATYYC   FQGSFYPFT   FGGGTKVEIK     106
               CDR L3

B

QVTLRESGPA LVKPTQTLTL TCTFSGFSLS TPGMSVG WIR     40
                                            CDR H1

QPPGKALEWL A DIWWDDKKDYNPSLKS RLT ISKDTSKNQV     80
                     CDR H2

VLKVTNMDPA DTATYYCAR SMITNFYFDV W GQGTTVTVSS     120
                            CDR H3

DIQMTQSPST LSASVGDRVT ITC SASSSVGYMH WYQQKPG     40
                                              CDR L1

KAPKLLIY   DTFKLAS   GVPSR   FSGSGSGTEF   TLTISSLQPD     80
             CDR L2

DFATYYC   FQGSFYPFT   FGGGTKVEIK     106
            CDR L3

B

QVTLRESGPA LVKPTQTLTL TCTFSGFSLS TAGMSVG WIR     40
                                           CDR H1

QPPGKALEWL A DIWWDDKKDYNPSLKS RLT ISKDTSKNQV     80
                 CDR H2

VLKVTNMDPA DTATYYCAR SMITNFYFDV W GQGTTVTVSS     120
                         CDR H3

DIQMTQSPST LSASVGDRVT ITC <u>SASSSVGYMH</u> WYQQKPG     40
                                                          CDR L1

KAPKLLIY   <u>DTFKLAS</u>   GVPSR   FSGSGSGTEF   TLTISSLQPD     80
               CDR L2

DFATYYC   <u>FQGSYYPFT</u>   FGGGTKVEIK     106
             CDR L3

B

QVTLRESGPA   LVKPTQTLTL   TCTFSGFSLS   <u>TAGMSVG</u>   WIR     40
                                                                                  CDR H1

QPPGKALEWL A <u>DIWWDDKKDYNPSLKS</u> RLT ISKDTSKNQV     80
                         CDR H2

VLKVTNMDPA DTATYYCAR <u>SMITNFYFDV</u> W GQGTTVTVSS     120
                                CDR H3

SEQUENCE LISTING

```
<160> NUMBER OF SEQ ID NOS: 26

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Mouse human
      chimeric antibody light chain variable chain

<400> SEQUENCE: 1

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
             20                  25                  30

His Trp Tyr Gln Gln Lys Pro Gly Lys Ala Pro Lys Leu Leu Ile Tyr
         35                  40                  45

Asp Thr Ser Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys
            100                 105

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Mouse human
      chimeric antibody heavy chain variable chain

<400> SEQUENCE: 2

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
     50                  55                  60

Leu Lys Ser Arg Leu Thr Ile Ser Lys Asp Thr Ser Lys Asn Gln Val
 65                  70                  75                  80
```

```
Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Gln
            100                 105                 110

Gly Thr Thr Val Thr Val Ser Ser
        115                 120

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Amino acid
      sequence of complementarity determining region L1
      of reference anti-RSV antibody

<400> SEQUENCE: 3

Ser Ala Ser Ser Ser Val Gly Tyr Met His
 1               5                  10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Amino acid
      sequence of complementarity determining region L2
      of reference anti-RSV antibody

<400> SEQUENCE: 4

Asp Thr Ser Lys Leu Ala Ser
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Amino acid
      sequence of complementarity determining region L3
      of reference anti-RSV antibody

<400> SEQUENCE: 5

Phe Gln Gly Ser Gly Tyr Pro Phe Thr
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Amino acid
      sequence of complementarity determining region H1
      of reference anti-RSV antibody

<400> SEQUENCE: 6

Thr Ser Gly Met Ser Val Gly
 1               5

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Amino acid
      sequence of complementarity determining region H2
      of reference anti-RSV antibody
```

```
<400> SEQUENCE: 7

Asp Ile Trp Trp Asp Asp Lys Lys Asp Tyr Asn Pro Ser Leu Lys Ser
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Amino acid
      sequence of complementarity determining region H3
      of reference anti-RSV antibody

<400> SEQUENCE: 8

Ser Met Ile Thr Asn Trp Tyr Phe Asp Val
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 9

Thr Ala Gly Met Ser Val Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 10

Thr Pro Gly Met Ser Val Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 11

Ser Met Ile Thr Asn Phe Tyr Phe Asp Val
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 12

Asp Thr Phe Lys Leu Ala Ser
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 13

Asp Thr Tyr Lys Leu Ala Ser
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 14

Phe Gln Gly Ser Phe Tyr Pro Phe Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 15

Phe Gln Gly Ser Tyr Tyr Pro Phe Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Amino acid
      sequence present in high affinity complementarity
      determining regions of antibodies of the invention

<400> SEQUENCE: 16

Phe Gln Gly Ser Trp Tyr Pro Phe Thr
 1               5

<210> SEQ ID NO 17
<211> LENGTH: 106
<212> TYPE: PRT
<213> ORGANISM: Artificial Sequence
<220> FEATURE:
<223> OTHER INFORMATION: Description of Artificial Sequence: Amino acid
      sequence of light chain variable region of clone 1
      of Figure 3A

<400> SEQUENCE: 17

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
             20                  25                  30
```

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Phe Tyr Pro Phe Thr
                85                  90                  95

Phe Gly Gly Gly Thr Lys Val Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Amino acid
      sequence of heavy chain variable region of clone 1
      of Figure 3B

<400> SEQUENCE: 18

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Gln
            100                 105                 110

Gly Thr Thr Val Thr Val Ser Ser
        115                 120

<210> SEQ ID NO 19
<211> LENGTH: 106
<212> TYPE: PRT
<213> ORGANISM: Artificial Sequence
<220> FEATURE:
<223> OTHER INFORMATION: Description of Artificial Sequence: Amino acid
      sequence of light chain variable region of clone 2
      of Figure 4A

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr

```
                85                  90                  95
Phe Gly Gly Gly Thr Lys Val Glu Ile Lys
            100                 105

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Amino acid
      sequence of heavy chain variable region of clone 2
      of Figure 4B

<400> SEQUENCE: 20

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Phe Tyr Phe Asp Val Trp Gly Gln
            100                 105                 110

Gly Thr Thr Val Thr Val Ser Ser
        115                 120

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Amino acid
      sequence of light chain variable region of clone 3
      of Figure 5A

<400> SEQUENCE: 21

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
             20                  25                  30

His Trp Tyr Gln Gln Lys Pro Gly Lys Ala Pro Lys Leu Leu Ile Tyr
         35                  40                  45

Asp Thr Phe Lys Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Phe Tyr Pro Phe Thr
                 85                  90                  95

Phe Gly Gly Gly Thr Lys Val Glu Ile Lys
            100                 105

<210> SEQ ID NO 22
<211> LENGTH: 120
<212> TYPE: PRT
<213> ORGANISM: Artificial Sequence
```

```
<220> FEATURE:
<223> OTHER INFORMATION: Description of Artificial Sequence: Amino acid
      sequence of heavy chain variable region of clone 3
      of Figure 5B

<400> SEQUENCE: 22

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Gln
            100                 105                 110

Gly Thr Thr Val Thr Val Ser Ser
        115                 120

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Amino acid
      sequence of light chain variable region of clone
      22 of Figure 6A

<400> SEQUENCE: 23

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Phe Tyr Pro Phe Thr
                85                  90                  95

Phe Gly Gly Gly Thr Lys Val Glu Ile Lys
            100                 105

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Amino acid
      sequence of heavy chain variable region of clone
      22 of Figure 6B

<400> SEQUENCE: 24

Gln Val Thr Leu Arg Glu Ser Gly Pro Ala Leu Val Lys Pro Thr Gln
 1               5                  10                  15
```

-continued

```
Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
50                      55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Gln
                100                 105                 110

Gly Thr Thr Val Thr Val Ser Ser
            115                 120
```

<210> SEQ ID NO 25
<211> LENGTH: 106
<212> TYPE: PRT
<213> ORGANISM: Artificial Sequence
<220> FEATURE:
<223> OTHER INFORMATION: Description of Artificial Sequence: Amino acid
    sequence of light chain variable region of clone
    23 of Figure 7A

<400> SEQUENCE: 25

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Tyr Tyr Pro Phe Thr
                85                  90                  95

Phe Gly Gly Gly Thr Lys Val Glu Ile Lys
            100                 105
```

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Amino acid
    sequence of heavy chain variable region of clone
    23 of Figure 7B

<400> SEQUENCE: 26

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
```

-continued

```
65                  70                  75                  80
Val Leu Lys Val Thr Asn Met Asp Pro Ala Asp Thr Ala Thr Tyr Tyr
                85                  90                  95
Cys Ala Arg Ser Met Ile Thr Asn Phe Tyr Phe Asp Val Trp Gly Gln
            100                 105                 110
Gly Thr Thr Val Thr Val Ser Ser
            115             120
```

ULTRA HIGH AFFINITY NEUTRALIZING ANTIBODIES

This application is a continuation of U.S. Ser. No. 09/771,415, filed Jan. 26, 2001 (now U.S. Pat. No. 6,656,467), which claims the benefit of U.S. Provisional Application Ser. No. 60/178,426, filed Jan. 27, 2000, the disclosure of each of which is hereby incorporated by reference in its entirety.

BACKGROUND OF THE INVENTION

The present invention relates to novel ultra high affinity neutralizing antibodies.

The current incidence of infection caused by resistant or difficult to control microbes has created a need for newer approaches to controlling such organisms, as well as to treating those already infected.

Among the more difficult infectious agents to control and treat are the viruses. For example, respiratory syncytial virus (RSV) is the major cause of acute respiratory illness in young children admitted to hospitals and the major cause of lower respiratory tract infection in young children. A major obstacle to producing an effective vaccine against such agents as RSV has been the issue of safety. Conversely, the use of immunoglobulins against such viral agents has proven of some value. For example, studies have shown that high-titred RSV immunoglobulin was effective both in prophylaxis and therapy for RSV infections in animal models.

An alternative approach has been the development of antibodies, especially neutralizing monoclonal antibodies, with high specific neutralizing activity. One drawback to this route has been the need to produce human antibodies rather than those of mouse or rat and thus minimize the development of human anti-mouse or anti-rat antibody responses, which potentially results in further immune pathology.

An alternative approach has been the production of human-murine chimeric antibodies in which the genes encoding the mouse heavy and light chain variable regions have been coupled to the genes for human heavy and light chain constant regions to produce chimeric, or hybrid, antibodies.

In some cases, mouse CDRs have been grafted onto human constant and framework regions with some of the mouse framework amino acids being substituted for correspondingly positioned human amino acids to provide a "humanized" antibody. [Queen, U.S. Pat. Nos. 5,693,761 and 5,693,762]. However, such antibodies contain intact mouse CDR regions and have met with mixed effectiveness, producing affinities often no higher than $10^7$ to $10^8$ $M^{-1}$.

A humanized anti-RSV antibody with good affinity has been prepared and is currently being marketed. [See: Johnson, U.S. Pat. No. 5,824,307]

The production of ultra high affinity antibodies would be desirable from the point of view of both the neutralizing ability of such an antibody as well as from the more practical aspects of needing to produce less antibody in order to achieve a desirable degree of clinical effectiveness, thereby cutting costs of production and/or allowing a greater degree of clinical effectiveness for administration in the same volume.

BRIEF SUMMARY OF THE INVENTION

The present invention relates to high affinity neutralizing antibodies and active fragments thereof exhibiting affinity constants of at least $10^{10}$ $M^{-1}$, and even $10^{11}$ $M^{-1}$, and more specifically to such a neutralizing monoclonal immunoglobulin, including antibodies and/or active fragments thereof, wherein the antibody and/or fragment has human constant regions.

The present invention solves the above-mentioned problems by providing high affinity neutralizing antibodies without the presence of intact mouse CDR regions that cause human anti-mouse antibody reactions (HAMA) and with sufficiently high affinity neutralizing activity to reduce cost and efficacy of overall production.

One aspect of the present invention relates to high affinity neutralizing antibodies with affinity constants of at least $10^{10}$ $M^{-1}$, and even $10^{11}$ $M^{-1}$, and with specificity towards specific antigenic determinants, such as those exhibited by virus-expressed proteins.

One object of the present invention is to provide such high affinity neutralizing antibodies with specificity toward antigens produced by viruses, such as where such antigens are expressed by virus-infected cells in a mammal, especially a human.

In one such embodiment, the high affinity neutralizing immunoglobulin, including antibodies and/or active fragments thereof, of the present invention, and active fragments thereof, are specific for respiratory syncytial virus (RSV), most especially for the F antigen expressed by said RSV and also expressed on the surfaces of cells infected with RSV (the presence of which antigen on the cell surface causes fusion of the cells into syncytia), Thus, in one embodiment, a high affinity neutralizing immunoglobulin, including antibodies and/or active fragments thereof, of the present invention binds to the same epitope on RSV as the antibody whose light chain variable chain has the sequence of SEQ ID NO: 1 (shown in FIG. 1A) and whose heavy chain variable chain has the sequence of SEQ ID NO: 2 (shown in FIG. 1B).

It is an object of the present invention to provide ultra high affinity neutralizing antibodies having substantially the framework regions of the immunoglobulin disclosed in FIG. 1 (with the same specificity of that immunoglobulin, which is an anti-RSV antibody structure) but wherein the immunoglobulins, including antibodies and active fragments thereof, of the present invention contain one or more CDRs (complementarity determining regions) whose amino acid sequences are independent of those in the so-called reference antibody, although said sequences may, in some cases, differ by no more than one amino acid and this may be limited to a difference in only one of said CDR regions.

In a preferred embodiment of the present invention, the novel immunoglobulins of the present invention will differ from the antibody of FIG. 1 (hereafter, the "basic antibody" or "reference antibody" or "reference immunoglobulin") only in the sequences of one or more of the CDRs and, in a most preferred embodiment these differences occur only in CDRs L2, L3, H1, and H3.

Especially preferred embodiments of the present invention have the framework sequences depicted in FIG. 1, thus having the heavy and light chain variable sequences depicted in FIGS. 3, 4, 5, 6, and 7.

In one embodiment, the high affinity neutralizing antibodies of the invention include a human constant region.

In a preferred embodiment, a high affinity RSV-neutralizing antibody of the invention, including active fragments thereof, with an affinity constant ($K_a$) of at least as high as $10^{10}$ $M^{-1}$, and even $10^{11}$ $M^{-1}$, is a recombinant immunoglobulin, such as an antibody or active fragment thereof, that includes a human constant region and framework regions for the heavy and light chains wherein at least a portion of the framework is derived from a human antibody (or from a consensus sequence of a human antibody framework), an example of said framework regions depicted for the antibody sequences of FIG. 1.

In one embodiment, all of the framework is derived from a human antibody (or a human consensus sequence).

In another highly specific embodiment, a high affinity RSV-neutralizing antibody, with an affinity of at least $10^{10}$ $M^{-1}$, is a recombinant antibody having a human constant region, one or more CDRs that are derived from a non-human antibody in which at least one of the amino acids in at least one of the CDRs is changed and in which all or a portion of the framework is derived from a human antibody (or a consensus sequence of a human antibody framework).

In a separate embodiment, a humanized neutralizing immunoglobulin that binds to the same epitope as the basic or reference antibody or immunoglobulin whose variable chains are shown in FIG. 1, and that has an affinity of at least $10^{11}$ $M^{-1}$, includes at least one of the following amino acids at the following positions of the CDRs: an alanine at position 2 of CDR H1, a phenylalanine at position 6 of CDR H3, a phenylalanine at position 3 of CDR L2, and a phenylalanine at position 5 of CDR L3. Other embodiments comprise other single amino acid substitutions at these locations.

It is another object of the present invention to provide compositions comprising the immunoglobulins disclosed herein wherein said structures are suspended in a pharmacologically acceptable diluent or excipient.

It is a still further object of the present invention to provide methods of preventing and/or treating respiratory syncytial virus comprising the administering to a patient at risk thereof, or afflicted therewith, of a therapeutically effective amount of a composition containing an immunoglobulin of the invention, such as where said antibodies or active fragments thereof exhibit the specificity and affinity properties disclosed herein for the immunoglobulins of the invention.

DEFINITIONS

The term "antigen" refers to a structure, often a polypeptide or protein, present on the surface of a microorganism, such as a virus, for which an antibody has affinity and specificity.

The term "antigenic determinant" refers to a specific binding site on an antigenic structure for which an immunoglobulin, such as an antibody, has specificity and affinity. Thus, a particle, such as a virus, may represent an antigen but may have on its surface a number of separate, and different, antigenic sites such as where the virus has a number of different surface proteins and each represents a distinct potential binding site for an immunoglobulin.

The term "immunoglobulin" refers to a protein or polypeptide having specificity and affinity for an antigen or antigenic determinant. This term includes antibodies, commonly depicted as tetrameric, as well as active fragments thereof, such fragments having specificity and affinity for antigens or antigenic determinants. Thus, "immunoglobulin" as used herein includes antibodies and all active fragments thereof.

The term "antibody" refers to a protein or polypeptide having affinity for an antigenic determinant, usually one found on the surface of a microorganism, especially a virus. Such an antibody is commonly composed of 4 chains and is thus tetrameric.

The term "neutralizing immunoglobulin" or "neutralizing antibody" refers to the ability of the immunoglobulins, including antibodies, of the present invention to reduce the replication of microorganisms, especially viruses, in organisms as well as in cell cultures. An indication of such ability is the data from the microneutralization assays disclosed hereinbelow. Such a structure usually has both variable and constant regions whereby the variable regions are mostly responsible for determining the specificity of the antibody and will comprise complementarity determining regions (CDRs).

The term "complementarity determining region" or "CDR" refers to variable regions of either H (heavy) or L (light) chains contains the amino acid sequences capable of specifically binding to antigenic targets. These CDR regions account for the basic specificity of the antibody for a particular antigenic determinant structure. Such regions are also referred to as "hypervariable regions."

The term "active fragment" refers to a portion of an antibody that by itself has high affinity for an antigenic determinant and contains one or more CDRs accounting for such specificity. Non-limiting examples include Fab, F(ab)'$_2$, heavy-light chain dimers, and single chain structures, such as a complete light chain or complete heavy chain.

The term "specificity" refers to the ability of an antibody to bind preferentially to one antigenic site versus a different antigenic site and does not necessarily imply high affinity.

The term "affinity" refers to the degree to which an antibody binds to an antigen so as to shift the equilibrium of antigen and antibody toward the presence of a complex formed by their binding. Thus, where an antigen and antibody are combined in relatively equal concentration, an antibody of high affinity will bind to the available antigen so as to shift the equilibrium toward high concentration of the resulting complex.

The term "affinity constant" refers to an association constant used to measure the affinity of an antibody for an antigen. The higher the affinity constant the greater the affinity of the immunoglobulin for the antigen or antigenic determinant and vice versa. An affinity constant is a binding constant in units of reciprocal molarity. Such a constant is readily calculated from the rate constants for the association-dissociation reactions as measured by standard kinetic methodology for antibody reactions.

BRIEF DESCRIPTION OF THE DRAWINGS

FIG. 1 shows the amino acid sequence of the light and heavy chain variable regions of an anti-RSV antibody wherein the CDR regions are underlined while non-underlined residues form the framework regions of the variable regions of each chain. In this antibody, the CDRs are derived from a mouse anti-RSV antibody while the framework regions consist mostly of sequences derived from a human antibody. For each CDR, locations at which amino acid replacements were used to achieve the high affinity CDRs and antibodies disclosed herein are in bold face. In accordance with the disclosure herein, such replacements were only in CDRs L2, L3, H1 and H3. FIG. 1A shows the light chain variable region (SEQ ID NO: 1) and FIG. 1B shows the heavy chain variable region (SEQ ID NO: 2) of the light and heavy chains, respectively. Constant region sequences are not shown. These sequences are present in the basic clone (see Table 2), designated IX-493 throughout this disclosure (i.e., SWSG—meaning a serine (S) at the key position (see tables 1 and 3) of high affinity CDR H1, a tryptophan (W) at the key position of high affinity CDR H3, a serine (S) at the key position of high affinity CDR L2, and a glycine (G) at the key position of high affinity CDR L3). For purposes of this disclosure, this is the "reference antibody."

FIG. 3 shows the heavy (panel B—SEQ ID NO: 18) and light (panel A—SEQ ID NO: 17) chain variable regions for the preferred embodiment of clone 1 (Table 2) of the invention disclosed herein. CDR regions are underlined while the amino acid differences versus the antibody of FIG. 1 are indicated in bold face. Thus, this preferred (i.e., high affinity) antibody has several of the high affinity CDRs (Table 3) present which give rise to higher affinity (over $10^{10}$ $M^{-1}$) than the basic or reference antibody.

FIG. 4 shows the heavy (panel B—SEQ ID NO: 20)and light (panel A—SEQ ID NO: 19) chain variable regions for the preferred embodiment of clone 2 (Table 2) of the invention disclosed herein. CDR regions are underlined while the amino acid differences versus the antibody of FIG. 1 are indicated in bold face. Thus, this preferred (i.e., high affinity) antibody has several of the high affinity CDRs (Table 3) present which give rise to higher affinity (over $10^{10}$ $M^{-1}$) than the basic or reference antibody.

FIG. 5 shows the heavy (panel B—SEQ ID NO: 22) and light (panel A—SEQ ID NO: 21) chain variable regions for the preferred embodiment of clone 3 (Table 2) of the invention disclosed herein. CDR regions are underlined while the amino acid differences versus the antibody of FIG. 1 are indicated in bold face. Thus, this preferred (i.e., high affinity) antibody has several of the high affinity CDRs (Table 3) present which give rise to higher affinity (over $10^{10}$ $M^{-1}$) than the basic or reference antibody.

FIG. 6 shows the heavy (panel B—SEQ ID NO: 24) and light (panel A—SEQ ID NO: 23) chain variable regions for the most preferred embodiment of clone 22 (Table 4) of the invention disclosed herein. CDR regions are underlined while the amino acid changes versus the antibody of FIG. 1 are indicated in bold face. Thus, this most preferred (i.e., highest affinity) antibody has several of the high affinity CDRs (Table 3) present which give rise to higher affinity (over $10^{11}$ $M^{-1}$) than the basic or reference antibody).

FIG. 7 shows the heavy (panel B—SEQ ID NO: 26)and light (panel A—SEQ ID NO: 25) chain variable regions for the preferred embodiment of clone 23 (Table 4) of the invention disclosed herein. CDR regions are underlined while the amino acid changes versus the antibody of FIG. 1 are indicated in bold face. Thus, this preferred (i.e., highest affinity) antibody, has several of the high affinity CDRs (Table 3) present which give rise to higher affinity (over $10^{11}$ $M^{-1}$) than the basic or reference antibody).

DETAILED DESCRIPTION OF THE INVENTION

Figure 2:
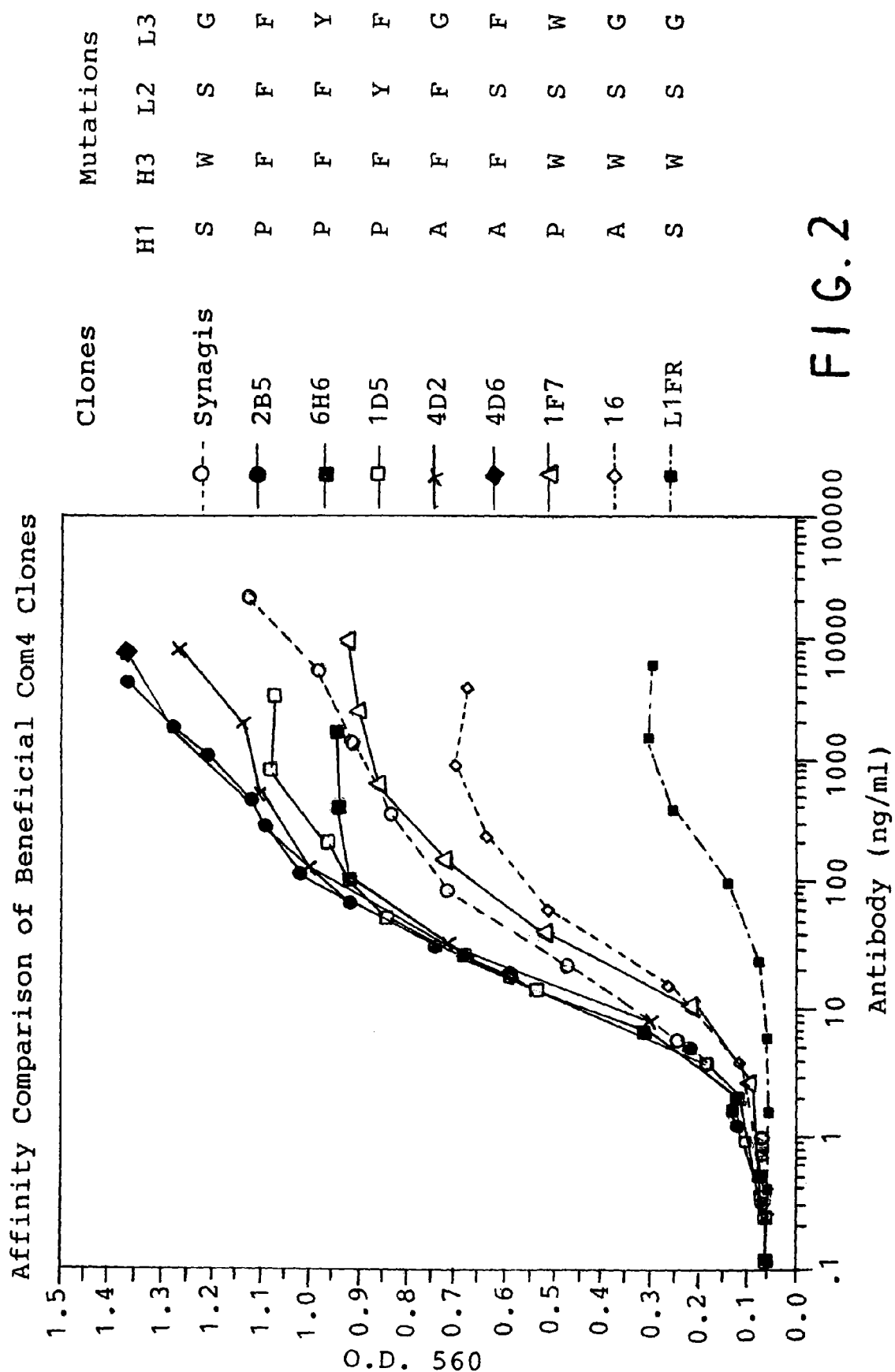
FIG. 2 shows affinity comparisons for a particular set of beneficial or high affinity clones. The clonal designations are on the left of the legend at the right of the drawing along with the indicated substitutions at CDRs H1, H3, L2, and L3 shown on the right of the legend. Measurements are by ELISA (OD at 560 nm shown on the left axis). Clone L1FR represents the results for the reference antibody structure of FIG. 1.

The present invention is directed to ultra high affinity neutralizing antibodies and active fragments thereof having affinity constants of at least $10^{10}$ $M^{-1}$. Active fragments of these antibodies are fragments containing at least one high affinity complementarity determining region (CDR).

With the advent of methods of molecular biology and recombinant technology, it is now possible to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with in vitro assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the immunoglobulins, or how they are recombinantly constructed, or how they are synthesized, in vitro or in vivo, using transgenic animals, such as cows, goats and sheep, using large cell cultures of laboratory or commercial size, in bioreactors or by direct chemical synthesis employing no living organisms at any stage of the process, all immunoglobulins have a similar overall 3 dimensional structure. In the case of an antibody, this structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity.

The variable region of either H or L chains contains the amino acid sequences capable of specifically binding to antigenic targets. Within these sequences are smaller sequences dubbed "hypervariable" because of their extreme variability between antibodies or active fragments of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains. The accepted CDR regions have been described by Kabat et al, *J. Biol. Chem.* 252:6609-6616 (1977). The numbering scheme is shown in the figures, where the CDRs are underlined and the numbers follow the Kabat scheme.

In all mammalian species, antibody polypeptides contain constant (i.e., highly conserved) and variable regions, and, within the latter, there are the CDRs and the so-called "framework regions" made up of amino acid sequences within the variable region of the heavy or light chain but outside the CDRs.

The immunoglobulins disclosed according to the present invention afford extremely high affinity (on the order of $10^{10}$ $M^{-1}$, and even $10^{11}$ $M^{-1}$, for the affinity constant, or $K_a$, defined as an association constant describing the binding of antibody and antigen as the ligands) for epitopes, or antigenic determinants, found in macromolecules, especially proteins, and most especially proteins expressed by viruses and other microorganisms, such as proteins expressed on the surfaces of viruses as well as the surfaces of cells infected with a virus. The high affinity antibodies of the present invention are neutralizing antibodies and thus reduce the replication of viruses in organisms as well as in cell cultures while maintaining sufficient homology to the antibody amino acid sequences of the recipient so as to prevent adverse immunological pathology. The latter feature is achieved through the use of constant regions similar to those of the recipient organism, such as a mammal and most especially a human. This feature is also achieved through the use of framework amino acid sequences similar, if not identical, to those found in antibodies from the recipient organism. In the latter case, some amino acid replacements may be made in the framework sequences so as to facilitate and maintain the high affinity interaction between the novel CDRs of the present invention and the antigen for which said antibodies show specificity.

As used herein, terms such as "antibody" and "active fragment" or "fragment" are not to be considered limiting in determining the full extent of the present invention. Thus, the fact that the term "antibody" is used rather than "active fragment" or "immunoglobulin" is not to be taken as a limitation on the invention or its uses so long as the requisite properties of specificity and affinity are exhibited by said structure.

In accordance with the invention disclosed herein, the affinity constants characterizing the affinities of the high affinity neutralizing antibodies, and active fragments thereof, of the present invention are association constants and were measured by the kinetics of antigen-antibody complex formation, with the rate constant for association to form the complex being denoted as $k_{assoc}$ or $k_{on}$ and the dissociation constant being denoted as $k_{diss}$ or $k_{off}$. Measurement of such constants is well within the ordinary skill in the art and the details will not be described further herein except for general methodology and specific conditions, where appropriate, as recited in the examples given herein to further describe the invention.

The high affinity antibodies of the present invention can be achieved, as already described, through genetically engineering appropriate antibody gene sequences, i.e., amino acid sequences, by arranging the appropriate nucleotide sequences and expressing these in a suitable cell line. Any desired nucleotide sequences can be produced using the method of codon based mutagenesis, as described, for example, in U.S. Pat. Nos. 5,264,563 and 5,523,388. Such procedures permit the production of any and all frequencies of amino acid residues at any desired codon positions within an oligonucleotide. This can include completely random substitutions of any of the 20 amino acids at an desired position or in any specific subset of these. Alternatively, this process can be carried out so as to achieve a particular amino acid a desired location within an amino acid chain, such as the novel CDR sequences according to the invention. In sum, the appropriate nucleotide sequence to express any amino acid sequence desired can be readily achieved and using such procedures the novel CDR sequences of the present invention can be reproduced. This results in the ability to synthesize polypeptides, such as antibodies, with any desired amino acid sequences. For example, it is now possible to determine the amino acid sequences of any desired domains of an antibody of choice and, optionally, to prepare homologous chains with one or more amino acids replaced by other desired amino acids, so as to give a range of substituted analogs.

In applying such methods, it is to be appreciated that due to the degeneracy of the genetic code, such methods as random oligonucleotide synthesis and partial degenerate oligonucleotide synthesis will incorporate redundancies for codons specifying a particular amino acid residue at a particular position, although such methods can be used to provide a master set of all possible amino acid sequences and screen these for optimal function as antibody structures or for other purposes. Such methods are described in Cwirla et al, *Proc. Natl. Acad. Sci.* 87:6378-6382 (1990) and Devlin et al., *Science* 249:404-406 (1990).

In accordance with the invention disclosed herein, enhanced antibody variants can be generated by combining in a single polypeptide structure one, two or more novel CDR sequences according to the invention, each shown to independently result in enhanced binding activity. In this manner, several novel amino acids sequences can be combined into one antibody, in the same or different CDRs, to produce high affinity antibodies within the present invention. For example, 3 such novel CDR sequences may be employed and the resulting antibodies screened for affinity for a particular antigenic structure, such as the F antigen or RSV. The overall result would thus be an iterative process of combining various single amino acid substitutions and screening the resulting antibodies for antigenic affinity in a step by step manner. Such methods were used to prepare some of the antibodies embodied within the present invention. Such methods also represent a convenient, if tedious, means of optimizing the antibody sequences of the present invention, especially the sequences of the CDR regions of said antibodies.

Using the novel sequences and methods of the present invention, such an approach avoids the time and expense of generating and screening all possible permutations and combinations of antibody structure in an effort to find the antibody with the maximum efficiency. Conversely, complete randomization of a single 10 amino acid residue CDR would generate over 10 trillion variants, a number virtually impossible to screen.

This iterative method can be used to generate double and triple amino acid replacements in a stepwise process so as to narrow the search for antibodies having higher affinity.

Conversely, it should be recognized that not all locations within the sequences of the different antibody domains may be equal. Substitutions of any kind in a particular location may be helpful or detrimental. In addition, substitutions of certain kinds of amino acids at certain locations may likewise be a plus or a minus as it affects affinity for the particular antigen. For example, it may not be necessary to try all possible hydrophobic amino acids at a given position. It may be that any hydrophobic amino acid will do as well. Alternatively, an acidic or basic amino acid at a given location may provide large swings in measured affinity. It is therefore necessary also to learn the "rules" of making such substitutions but the determination of such "rules" may not require the study of all possible combinations and substitutions—trends may become apparent after examining fewer than the maximum number of substitutions.

In accordance with the foregoing, the antibodies of the present invention are ultra high affinity neutralizing antibodies, such as anti-RSV antibodies, and in the latter case most preferably antibodies with specificity toward the same epitope of RSV as the antibody of U.S. Pat. No. 5,824,307.

In addition, the affinities of the ultra high affinity antibodies of the invention typically are at least $10^{10}$ $M^{-1}$. Because such high affinities are not easily measured, except by the procedures described herein, such value may commonly be considered as part of a range and may, for example, be within 2 fold of $10^{10}$ $M^{-1}$ or be greater than $10^{10}$ $M^{-1}$ or may even be numerically equal to $10^{10}$ $M^{-1}$. In such cases, the affinity is denoted by an affinity constant, which is in the nature of a binding constant so as to give units of reciprocal molarity. As such, the affinity of the antibody for antigen is proportional to the value of this constant (i.e., the higher the constant, the greater the affinity). Such a constant is readily calculated from the rate constants for the association-dissociation reactions as measured by standard kinetic methodology for antibody reactions.

In a specific embodiment, the high affinity neutralizing antibodies of the present invention, and active fragments thereof, have affinity constants for their respective antigens of at least at least $10^{11}$ $M^{-1}$, in some cases being in excess of this value, a range at the very upper region of measurability.

The high affinity neutralizing antibodies of the present invention, and active fragments thereof, may be advantageously directed to any antigenic determinants desired, such as epitopes present on any type of macromolecule, especially peptide epitopes present as part of the three dimensional structure of protein and polypeptide molecules. Such peptide epitopes may commonly be present on the surfaces, or otherwise be part of the structure of, microorganisms and cells, such as cancer cells. Microorganisms expressing such peptide epitopes includes bacteria and viruses. In the latter case, the proteins and polypeptides exhibiting peptide epitopes may be molecules expressed on the surfaces of the virus or may be expressed by cells infected with a virus. For purposes of evaluating the efficacy of the rules and methods disclosed according to the present invention, a virus was chosen as one available antigenic source for developing antibodies within the present invention. The virus chosen for further analysis was the respiratory syncytial virus (RSV). This latter virus was chosen because it is well characterized with respect to its replicative cycle as well as with respect to the antigenic determinants found on its surface. In addition, antigens known to be expressed by cells infected with this virus are well characterized. Thus, the virus exhibits both a surface G antigen and a surface F antigen, both proteins. The G antigen facilitates binding of the virus to cell surfaces and the F proteins facilitates the fusion of the virus with cells. The cells so infected also express the F antigen on their surfaces and the latter result induces fusion of the cells to form a syncytium, hence the name of the virus. In addition, this virus is a convenient subject for analysis in that cell lines readily infected by this virus are well known and well characterized, thereby making it an easy virus to grow and culture in vitro. Further, antibodies available for treatment of this virus are known and are commercially available (for example, the antibodies disclosed in U.S. Pat. No. 5,824,307). For these reasons, the antibody disclosed in said patent, the disclosure of which patent is hereby incorporated by reference in its entirety, contains the amino acid sequences of the "reference antibody" disclosed in FIG. 1 and whose CDR sequences are summarized in Table 1. Thus, the availability of a commercially successful antibody product as well as the well characterized properties of RSV made this an ideal combination to use in testing and optimizing the antibodies of the present invention and the rules disclosed herein for producing high affinity CDRs for use in constructing such antibodies. Otherwise, the antibodies disclosed herein, as well as the methods disclosed herein for preparing such antibodies, are in no way limited to RSV as the antigen but are readily and advantageously applied generally to the field of antibody technology. In addition, even the specific embodiments provided by the present disclosure and which are directed specifically to antigenic determinants expressed by RSV, and cells infected with RSV, also may have high affinity for other epitopes, especially those present on related viruses. Therefore, as disclosed in accordance with the present invention, RSV, and the antibody with variable sequences as shown in FIG. 1, are merely a convenient model system used as a reference point for developing and applying the methods of antibody technology taught by the present invention.

A high affinity neutralizing antibody according to the present invention, including active fragments thereof, comprises at least one high affinity complementarity determining region (CDR) wherein said CDR has an amino acid sequence selected to result in an antibody having an affinity constant $(K_a)$ of at least $10^{10}$ $M^{-1}$. In preferred embodiments, such antibody, or active fragment, comprises at least 2 high affinity CDRs, or at least 3 high affinity CDRs or even at least 4 high affinity CDRs. In highly preferred embodiments, such antibodies or active fragments comprise 3 or 4 high affinity CDRs. In one preferred embodiment, such active fragment is an Fab fragment.

The high affinity antibodies of the present invention commonly comprise a mammalian, preferably a human, constant region and a variable region, said variable region comprising heavy and light chain framework regions and heavy and light chain CDRs, wherein the heavy and light chain framework regions are derived from a mammalian antibody, preferably a human antibody, and wherein the CDRs are derived from an antibody of some species other than a human, preferably a mouse. Where the framework amino acids are also derived from a non-human, the latter is preferably a mouse.

In addition, high affinity antibodies of the invention bind the same epitope as the antibody from which the CDRs are derived, and wherein at least one of the CDRs of said ultra high affinity antibody contains amino acid substitutions, and wherein said substitutions comprise the replacement of one or more amino acids in the CDR regions by non-identical amino acids, preferably the amino acids of the correspondingly aligned positions of the CDR regions of the human antibody contributing the framework and constant domains.

The high affinity CDRs may be produced by amino acid substitutions in non-high affinity CDRs to produce such high affinity CDRs or such high affinity CDRs may be synthesized directly to form such high affinity CDRs. Thus, the ultra high affinity neutralizing antibodies of the present invention may have amino acid substitutions in only one of the CDR regions, preferably more than one CDR region, and most preferably 3 or even 4 such regions, with possibly as many as 5 or even all 6 of the CDRs containing at least one substituted amino acid.

In applying the methods disclosed herein to produce antibodies of the present invention, the method of preparing the antibodies is not a limiting factor. Thus, the high affinity neutralizing antibodies of the present invention may be prepared by generating polynucleotide sequences coding for the polypeptides of the antibodies and using vectors to insert said polynucleotide sequences into permissive cells capable of not only expressing such polypeptides but also of assembling them into characteristic tetrameric antibody structures that are then retrieved from the cells or cell cultures, possibly being secreted into the medium by such cells. Technologies for such manufacturing procedures are already known and patented and are not essential to practicing the present invention. [see: Morrison et al, U.S. Pat. No. 5,807,715]. In addition, the polypeptide chains of the antibodies of the present invention may be synthesized chemically, with or without the addition of enzymes, and then chemically joined to form tetrameric structures of the usual $H_2L_2$ configuration. Thus, any method of preparing the antibodies disclosed herein can be utilized.

The present invention is also directed to the formation of high affinity neutralizing antibodies, with the properties already enumerated, having high affinity as a result predominantly of having high affinity CDR sequences. In accordance with the present invention, the CDR sequences of the antibodies disclosed herein have been optimized so as to confer upon the antibody molecule the ultra high affinities characteristic of the antibodies of the present invention. Such CDR sequences, together with the framework sequences disclosed herein, especially those taught by the sequences of FIGS. 1, 3, 4, 5, 6, and 7, and most especially when used with constant region sequences characteristic of the antibodies of the organism acting as recipient of the antibodies of the present invention when used therapeutically, produce the antibodies of the present invention in their more specific embodiments. However, the methods of the present invention are more specifically directed to the CDR amino acid sequences.

To produce immunoglobulins, such as antibodies and/or active fragments thereof, within the present invention, e.g., high affinity neutralizing antibodies, the rules taught by the present invention are used advantageously to produce antibody molecules whose structures incorporate the sequences of the high affinity CDR sequences disclosed according to the present invention. Thus, the high affinity neutralizing antibodies of the present invention are, in essence, not truly "monoclonal" antibodies as that term is commonly used, since they do not have to be produced by cloning anything. As already mentioned, the sequences of the antibodies of the invention may be directly synthesized and thus may not be identical to any antibody sequences, especially not to any CDR sequences, presently known. The sequences themselves can be wholly novel ab initio and not be exactly represented in any antibody produced by any living organism. Thus, the high affinity CDR sequences disclosed herein are found, or achieved, by optimization, as disclosed herein, and then, once said high affinity CDR sequences are known, can be used to synthesize fully functional antibody molecules, whether dimeric or tetrameric, bifunctional or monofunctional, by any and all means known to science.

In keeping with the foregoing, and in order to better describe the sequences disclosed according to the invention, including their optimization, the sequence of the light and heavy chain variable regions of a reference antibody (here, the anti-RSV antibody of U.S. Pat. No. 5,824,307) are shown in FIG. 1A (light chain variable region—SEQ ID NO: 1) and FIG. 1B (heavy chain variable region—SEQ ID NO: 2). Also in accordance with the invention, novel sequences were produced with amino acid differences only in CDR regions relative to the reference antibody. One means utilized to accomplish this result was to introduce mutations in CDR regions of the so-called starting or reference chains and then assay the resulting recombinatorial clones for antigen (RSV F protein) affinity.

In accordance with the forgoing, changes were made in first one CDR sequence to optimize that sequence and determine the "critical" residue, or residues, than said position(s) was optimized through a series of amino acid substitutions limited to that position alone. Each of the 6 CDRs of the antibody clone was studied in turn until the "critical" CDRs were determined (wherein "critical CDRs" means CDRs having a substantial effect on antibody binding, such as the beneficial or high affinity CDRs of Table 3). No all CDRs were found to be critical. For the antibody used in this particular study, only CDRs H1, H3, L2, and L3 were found to be critical but the results may be different for a different antibody. Once a "high affinity" CDR was determined (i.e., a "beneficial CDR") then combinations of the CDRs were studied to optimize the combination of CDR sequences resulting in a high affinity neutralizing antibody of the invention.

As a very specific embodiment, the invention disclosed herein relates to a high affinity neutralizing antibody against respiratory syncytial virus (RSV) having an affinity constant of at least $10^{10}$ $M^{-1}$, wherein said affinity constant could be within at least 2 fold of this value because of the variability of such determinations and the variability of affinity of the different cloned antibodies for the antigen (here, F antigen of RSV). Some of the resulting optimized structures within this embodiment had $K_a$ greater than $10^{11}$ $M^{-1}$ (for example, clones numbered 22 and 23 in Table 4).

This high affinity neutralizing antibody is also an antibody that binds to the same epitope on RSV as the antibody whose light chain variable region has the sequence of SEQ ID NO: 1 (FIG. 1A) and whose heavy chain variable region has the sequence of SEQ ID NO: 2 (FIG. 1B).

In general, the approach used to identify antibodies of the invention, based on the specific example of anti-RSV just described, was to generate nucleotide sequences for the genes expressing the desired antibody chains and insert these into vectors then used to transform *Escherichia coli* cells by standard protocols. The cells were grown in wells and the supernatant sampled and measured for antigen binding using capture lift and ELISA techniques. [See: Watkins et al, (1997) *Anal. Biochem.* 253, 37-45; Watkins et al, (1998) *Anal. Biochem.* 256, 169-177 (the specifications of which are incorporated herein by reference)] These polynucleotides were designed so as to provide single amino acid replacements in the CDRs that could then be screened for increased affinity, with beneficial replacements (those yielding increased affinity) being selectively combined for increased affinity. These were then screened for binding affinity for F antigen of RSV versus the basic or reference antibody.

Using this protocol, ELISA data indicated that no single amino acid replacements in CDRs L1 or H2 produced any increase in the affinity of the antibody clone for the epitope used as antigen (here, the F antigen of RSV). Therefore, the antibodies of the present invention all contain CDR sequences that differ from the reference antibody only in CDRs L2, L3, H1 and H3 (here, the reference antibody with sequences in FIG. 1 was merely a useful reference against which to test procedures for optimization of antibody affinity by increasing $K_a$ and any other system could be used equally well).

The antibodies thus disclosed herein with respect to RSV also commonly have framework regions derived from a human antibody but, where not so derived, preferably from a mouse.

For the CDRs of the reference antibody, the amino acid sequence of each CDR (as given in the sequences of FIG. 1) is shown in Table 1. Amino acid residue locations within the CDRs of the basic or reference antibody, which, if replaced by amino acids as taught by the present invention, following optimization, produced high affinity CDR sequences (resulting in very high affinity neutralizing antibodies) and thereby a beneficial result (increase in affinity) are indicated in bold face and underlining in Table 1 (such sequences giving increased affinity over the reference antibody being denoted as "beneficial CDRs" or "high affinity CDRs"). The CDRs of the basic or reference antibody (FIG. 1) are referred to herein as "basic or reference CDRs"). Thus, Table 1 represents the CDR sequences depicted in FIG. 1 (i.e., for the anti-RSV reference antibody used herein to monitor optimization).

TABLE 1

Sequences of Basic or Reference CDRs

| CDR | Length | Sequence | SEQ ID NO. |
|---|---|---|---|
| L1 | 10 | SASSSVGYMH | 3 |
| L2 | 7 | DT<u>S</u>KLAS | 4 |
| L3 | 9 | FQGS<u>G</u>YPFT | 5 |
| H1 | 7 | T<u>S</u>GMSVG | 6 |
| H2 | 16 | DIWWDDKKDYNPSLKS | 7 |
| H3 | 10 | SMITN<u>W</u>YFDV | 8 |

With respect to the sequences disclosed herein, the CDR regions as defined for purposes of the present invention are those segments corresponding to residues 24-33 (CDR L1), 49-55 (CDR L2) and 88-95 (CDR L3) of the light chain variable regions and residues 31-37 (CDR H1), 52-67 (CDR H2) and 100-109 (CDR H3) of the heavy chain variable regions of the antibodies disclosed herein.

In producing the antibodies of the present invention, whether by generating clones or cloning the polypeptide chains composing said antibodies, or by direct synthesis of the polypeptide sequences, with or without the use of polynucleotide sequences coding therefor, or by whatever method the user may choose, since no method of producing said antibodies results in a limitation of the teaching of the present invention, the basic or reference antibody (heavy and light chain variable regions (CDRs plus Framework) shown in FIG. 1) can be used as a "template" for generating the novel CDR sequences of the antibodies of the present invention and for purposes of comparing binding constants, etc. Standard approaches to characterizing and synthesizing the six CDR libraries of single mutations were used (see Wu et al, Proc. Natl. Acad. Sci. 95:6037-6042 (1998)). The target CDR was first deleted for each of the libraries prior to annealing the nucleotides. For synthesis of the libraries, the CDRs were defined as in Table 1. Codon based mutagenesis for oligonucleotide synthesis to yield the CDR sequences of the invention was employed (as described above).

Libraries were initially screened by capture lift to identify the highest affinity variants. Subsequently, these clones were further characterized using capture ELISA and by titration on immobilized antigen.

DNA from the highest affinity variants was sequenced to determine the nature of the beneficial or high affinity replacements. After screening, it was determined that eight beneficial or high affinity replacements, occurring in only four of the CDRs, had been observed. These are summarized as the CDR sequences in Table 3 with differences versus the reference or basic CDRs of Table 1 being bold and underlined. Thus, the CDR sequences of Table 3 can be considered a CDR library of cassettes available for use in producing a high affinity neutralizing antibody of the present invention where specificity is directed toward the F antigen of RSV.

Analysis of the data indicated that replacement of amino acids at selected locations had greatly increased epitope binding, especially where the nature of the replacement was the insertion of an amino acid selected from the group phenylalanine, alanine, proline, tryptophan and tyrosine, most especially phenylalanine, all such beneficial or high affinity replacements again being at selected positions.

For the optimization experiment described herein and employing the RSV/anti-RSV system, the most beneficial of high affinity CDRs were found to result from amino acid replacements in 3 or 4 of the 6 CDRs, and in just 4 amino acid locations overall. Thus, the high affinity neutralizing antibodies of the present invention contain amino acid sequences differing from that of the base or reference antibody only in complementarity determining regions, or in such regions as well as in surrounding framework regions, unlike previously known man-made antibodies. Thus, the antibodies of the present invention are high affinity neutralizing antibodies containing one or more CDR sequences selected so as to produce high affinity in the antibody molecule. In the specific embodiment using RSV as the target such differences are found only in L2 (or CDRL2), L3 (or CDRL3), H1 (or CDRH1) and H3 (or CDRH3). As noted, the greatest affinities for this antibody occurred only at selected amino acid positions of these CDRs, and in some of the embodiments of the present invention just one amino acid location in each CDR was preferred for giving high affinity.

Thus, for CDR H1, substitution at amino acid 2 of the CDR (counting from the amino terminal end of the particular underlined CDR sequence of FIG. 1B), especially by replacing the serine located at position 2 of CDR H1 of the basic or reference antibody with either an alanine or a proline, was found to be most beneficial and therefore to result in higher affinity for the RSV antigen epitope. For CDR H3, replacement of the glycine at position 6 of the CDR sequence, especially by either a phenylalanine or tryptophan, most especially by phenylalanine, was found to result in increased affinity for the RSV epitope. For CDR L2, replacement of the serine at position 3 of the CDR, especially by either a phenylalanine or a tyrosine, resulted in increased affinity for F antigen. For CDR L3, replacement of the glycine at position 5 of the CDR, especially by phenylalanine, tryptophan or tyrosine, resulted in increased affinity for the RSV epitope.

In accordance with the invention, by combining such amino acid substitutions so that more than one occurred in the same antibody molecule, it was possible to greatly increase the affinity of the antibodies disclosed herein for the epitope of the F antigen of RSV.

Table 2 shows the results of using the novel CDR sequences (for H1, H3, L2, and L3, respectively) of a number of clones according to the present invention. As shown in Table 2, a particular antibody may have incorporated therein as many as 1, 2, or 3 novel CDRs of the invention versus the basic or reference antibody chains shown in FIGS. 1A and 1B (for light (L2 and L3) and heavy (H1 and H3) chains, respectively). The effects of the novel CDRs are described in terms of Antigen (Ag) titration score (see below), where the basic or reference antibody is shown at the top and has a score of 0.1. Other scores are indicated relative to this 0.1 score of the "basic or reference antibody" sequences. The identities of the amino acids giving highest affinities at the respective locations (i.e., position 2 for H1, position 6 for H3, position 3 for L2, and position 5 for L3) are indicated below the amino acids for the basic or reference antibody merely to indicate the range of mutations used for each CDR.

The total number of clones examined in this experiment was 37, with some duplicates (indicated by the "n" value in parenthesis, for example, "n=4" for clone No. 7 indicates that 4 duplicate clones were examined).

In general, the data showed that there is a correlation between affinity and the number of beneficial or high affinity CDRs, with all of the higher affinity variants having more than one beneficial or high affinity CDR. Further, all of the best clones had an F (Phe) at position 6 within CDR H3. Also, the beneficial or high affinity CDRs were those wherein a hydrophobic, especially an aromatic, amino acid was inserted in place of the residue found in the basic or reference antibody.

The antibody titration assay employed varying concentrations of antibody using 500 ng of RSV F antigen for each measurement. A graph of comparison data for a number of the combinatorial clones of Table 2 is shown in FIG. 2.

In sum, Table 2 shows a number of clones evaluated by the procedures described herein along with the amino acids occurring at the key locations (underlined and bold-faced in Tables 1 and 3) of CDRs H1, H3, L2, and L3. The Table also summarizes the number of differences between the CDRs of these clones versus the corresponding CDRs of the reference antibody (See Table 1 and FIG. 1). The right side of the Table shows an "Ag Score" or antigen binding value, which represents an arbitrary and qualitative value, ranging from 0-4, and represents a qualitative estimate of the relative binding ability of the different antibody clones based on their respective titration curves. This value is provided here only for rough qualitative comparisons of the different antibodies and is not intended as a quantitative measure of binding ability.

TABLE 2

Summary of Clone Data

| Clone | CDRs | | | | # Novel CDRs | Ag Score |
|---|---|---|---|---|---|---|
| | H1 | H3 | L2 | L3 | | |
| Basic | S | W | S | G | 0 | 0.1 |
| Single | A | F | F | F | | |
| | P | | Y | W | | |
| | | | | Y | | |
| 1 | A | F | S | F | 3 | 4 |
| 2 | A | F | F | G | 3 | 4 |
| 3 (n = 3) | P | F | F | F | 4 | 4 |
| 4 (n = 3) | P | F | F | Y | 4 | 3.5 |
| 5 (n = 3) | P | F | F | W | 4 | 3.5 |

TABLE 2-continued

Summary of Clone Data

| Clone | CDRs | | | | # Novel CDRs | Ag Score |
|---|---|---|---|---|---|---|
| | H1 | H3 | L2 | L3 | | |
| 6 | P | F | Y | F | 4 | 3.5 |
| 7 (n = 4) | P | F | F | G | 3 | 3 |
| 8 | P | F | F | ? | 3+ | 3.5 |
| 9 (n = 2) | P | F | S | W | 3 | 3 |
| 10 | P | F | S | F | 3 | 3 |
| 11 | P | W | F | W | 3 | 3 |
| 12 (n = 2) | P | W | F | F | 3 | 2.5 |
| 13 (n = 3) | S | F | F | F | 3 | 2.5 |
| 14 | S | F | F | W | 3 | 2.5 |
| 15 (n = 2) | A | F | S | G | 2 | 2.5 |
| 16 (n = 2) | P | F | S | G | 2 | 2 |
| 17 | P | W | S | W | 2 | 2 |
| 18 (n = 2) | S | F | F | G | 2 | 2 |
| 19 | S | F | S | W | 2 | 2 |
| 20 | S | F | S | F | 2 | 2 |
| 21 | S | W | Y | F | 2 | 2 |

Table 2 also shows the number of novel CDRs for each antibody clone (meaning the number of CDRs in the antibody with at least one amino acid difference with respect to the corresponding CDR of the reference antibody—see Table 1). The number of novel CDRs is also the number of "beneficial" or "high affinity" CDRs present in that antibody molecule. The amino acid differences in the novel CDR would occur at the position bold and underlined in Table 1 for the reference antibody so that the amino acid bold and underlined in Table 1 has been replaced by the amino acid indicated for the respective CDR in Table 2 (using standard single letter amino acid designations).

The novel CDRs represented in each of the clones is readily determined by locating the clone in the table, and matching the indicated amino acid for each CDR with the corresponding amino acid for the same CDR next to the basic or reference clone. For convenience, where an amino acid is different in a particular CDR of one of the clones, the new amino acid is indicated in bold face. In addition, for all clones shown in the table, replacements occur only at the selected locations recited above as yielding a novel CDR. Thus, all substitutions in CDR H1 relative to the basic or reference antibody are at position 2 of the CDR (meaning, again, the second amino acid from the N-terminal end of CDR H1 as underlined and bold-faced in FIG. 1 and Tables 1 and 3), all substitutions in CDR H3 are at position 6, all substitutions in CDR L2 are at position 3, and all substitutions in CDR L3 are at positions 5, again all with reference to the basic or reference antibody. It should be kept in mind that the basic or reference antibody was chosen because it was known already to have a very high affinity for RSV-epitopes. [See: Johnson et al, (1997) *J. Infect. Dis.*, 176, 1215-1224] So, for example, the table shows that for clone No. 1, for the beneficial or high affinity CDR H1, an alanine is used in place of the serine at position 2 of CDR H1 of the basic or reference antibody, thereby achieving an increased affinity for RSV, and a phenylalanine occurs in place of the tryptophan at position 6 of CDR H3, the serine at position 3 of CDR L2 of the basic or reference antibody was used and a phenylalanine occurred at position 5 of beneficial or high affinity CDR L3.

Thus, the novel and beneficial CDRs according to the present invention (i.e., high affinity CDRs or CDR sequences whose presence in the basic or reference antibody in place of the corresponding basic or reference CDR served to greatly increase the affinity of said antibody for the same RSV epitope) which are present in the antibody structures produced in the supernatants tested for the clones of Table 2 are summarized in Table 3. In each case, the bold face indicates how the novel and beneficial, or high affinity, CDRs of the invention differ from the corresponding CDRs of the basic or reference anti-RSV antibody.

TABLE 3

Sequences for High Affinity CDRs

| CDR | Sequence | SEQ ID NO: |
|---|---|---|
| H1 | TAGMSVG | 9 |
| H1 | TPGMSVG | 10 |
| H3 | SMITNFYFDV | 11 |
| L2 | DTFKLAS | 12 |
| L2 | DTYKLAS | 13 |
| L3 | FQGSFYPFT | 14 |
| L3 | FQGSYYPFT | 15 |
| L3 | FQGSWYPFT | 16 |

While the CDR sequences of Table 3 represent the sequences for the high affinity CDRs disclosed according to the invention, it is understood that one or more of these CDRs may be present in the same antibody and the sequences of the table indicate the set from which appropriate sequences for each of the high affinity CDRs may be selected. Thus, as shown in Table 3, when a high affinity H1 CDR is present in a high affinity neutralizing antibody of the invention disclosed herein, it has a sequence corresponding to the sequence of SEQ ID NO: 9 or 10. When a neutralizing antibody of the claimed invention contains a high affinity H3 CDR, said CDR has the sequence of SEQ ID NO: 12. When a high affinity neutralizing antibody of the invention contains a high affinity L2 CDR, said high affinity L2 CDR has an amino acid sequence selected from the group consisting of the sequences of SEQ ID NO: 12 and 13. Finally, when a high affinity neutralizing antibody of the present invention contains a high affinity L3 CDR, said CDR has an amino acid sequence selected from the group consisting of the sequences of SEQ ID NO: 14, 15 and 16.

As already stated, in one embodiment, the high affinity neutralizing antibodies are antibodies that include a human constant region.

Thus, in a preferred embodiment, the high affinity neutralizing antibody of the invention, with an affinity of at least $10^{10}$ $M^{-1}$, or even at least $10^{11}$ $M^{-1}$, is a grafted antibody that includes a human constant region and a framework for the heavy and light chains wherein at least a portion of the framework is derived from a human antibody (or from a consensus sequence of a human antibody framework).

In another embodiment, all of the framework is derived from a human antibody (or a human consensus sequence).

Thus, an RSV-neutralizing antibody, with an affinity of at least $10^{10}$ $M^{-1}$, is a grafted antibody having a human constant region, one or more CDRs that are derived from a non-human antibody in which at least one of the amino acids in at least one of said CDRs is changed and in which all or a portion of the framework is derived from a human antibody (or a consensus sequence of a human antibody framework).

Because the combination of CDR sequences of one antibody with non-CDR regions of another antibody results from a form of "grafting" of CDRs onto the remainder of the molecule, these have been referred to as "CDR grafted" antibodies. Today, using the techniques of genetic engineering the same product can be formed without isolating any sequences from actual antibodies. So long as the desired CDR sequences, and the constant and framework sequence are known, genes with the desired sequences can be assembled and, using a variety of vectors, inserted into appropriate cells for expression of the functional tetrameric antibody molecules. Coupling this with the methodology already described permits the assembly of single mutation libraries wherein the antibodies possess the same sequences as corresponding grafted antibodies and, therefore, the same structure and binding affinities.

The high affinity antibodies of the invention can be present in a relatively pure or isolated form as well as in a supernatant drawn from cells grown in wells or on plates. Such supernatants were used to generate the data of Table 1. The antibodies of the invention can thus also be present in the form of a composition comprising the antibody of the invention and wherein said antibody is suspended in a pharmacologically acceptable carrier, or excipient. The antibodies of the invention may be present in such a composition at a concentration, or in an amount, sufficient to be of therapeutic or pharmacological value in treating diseases, such as RSV. Said antibodies may also be present in a composition in a more dilute form.

Consequently, the invention is also directed to providing a method of preventing and/or treating respiratory syncytial virus infections comprising the administering to a patient at risk thereof, or afflicted therewith, of a therapeutically (including prophylactically) effective amount of the antibody composition described herein.

One preferred embodiment of the high affinity antibodies of the present invention is the antibody whose heavy and light chain CDR regions have sequences as follows: CDR H1 has the sequence of SEQ ID NO: 9, CDR H3 has the sequence of SEQ ID NO: 11, CDR L2 has the sequence of SEQ ID NO: 4 (no change from CDR L2 of the reference sequence of FIG. 1A), and CDR L3 has the sequence of SEQ ID NO: 14 (see Table 3). In this preferred embodiment, the affinity constant is about $6.99 \times 10^{10}$ (or about 14.3 pM as a dissociation constant) as shown in Table 4 (clone 1). The heavy and light chain variable regions of an antibody comprising this embodiment, along with framework sequences, is shown in FIG. 3.

Another preferred embodiment of the high affinity antibodies of the present invention is the antibody whose heavy and light chain CDR regions have the sequences as follows: CDR H1 has the sequence of SEQ ID NO: 9, CDR H3 has the sequence of SEQ ID NO: 11, CDR L2 has the sequence of SEQ ID NO: 12, and CDR L3 has the sequence of SEQ ID NO: 5 (see Table 2, clone 2—no difference from the reference sequence of CDR L3 of FIG. 1A). In this preferred embodiment, the affinity constant is about $7.30 \times 10^{10}$ (or about 13.7 pM as a dissociation constant) as shown in Table 4 (clone 2). The heavy and light chain variable regions of an antibody comprising this embodiment, along with framework sequences, is shown in FIG. 4.

An additional preferred embodiment of the high affinity antibodies of the present invention is the antibody whose heavy and light chain CDR regions have the sequences as follows: CDR H1 has the sequence of SEQ ID NO: 10, CDR H3 has the sequence of SEQ ID NO: 11, CDR L2 has the sequence of SEQ ID NO: 12, and CDR L3 has the sequence of SEQ ID NO: 14 (see Table 3 for CDR sequences) which clone is designated number 3 in Table 2. In this preferred embodiment, the affinity constant is about $8.13 \times 10^{10}$ (or about 12.3 pM as a dissociation constant) as shown in Table 4 (clone 3).

The heavy and light chain variable regions of an antibody comprising this embodiment, along with framework sequences, is shown in FIG. 5.

A most preferred embodiment of the high affinity antibodies of the present invention is the antibody whose heavy and light chain CDR regions have the sequences as follows: CDR H1 has the sequence of SEQ ID NO: 9, CDR H3 has the sequence of SEQ ID NO: 11, CDR L2 has the sequence of SEQ ID NO: 12, and CDR L3 has the sequence of SEQ ID NO: 14 (see Table 3). In this preferred embodiment, the affinity constant is about $3.6 \times 10^{11}$ (or about 2.8 pM as a dissociation constant) as shown in Table 4 (clone 22). The heavy and light chain variable regions of an antibody comprising this embodiment, along with framework sequences, is shown in FIG. 6.

Another most preferred embodiment of the present invention is the antibody whose heavy and light chain CDR regions include the following sequences: CDR H1 has the sequence of SEQ ID NO: 9, CDR H3 has the sequence of SEQ ID NO: 11, CDR L2 has the sequence of SEQ ID NO: 12, and CDR L3 has the sequence of SEQ ID NO: 15 (see Table 3). In this latter preferred embodiment, the affinity constant is about $4 \times 10^{11}$ (about 2.5 pM as a dissociation constant) as shown in Table 4 (clone 23). The heavy and light chain variable regions of an antibody comprising this embodiment, along with framework sequences, is shown in FIG. 7.

In particularly preferred embodiments, the antibodies of the present invention will have the framework regions of the sequences depicted for the framework regions shown in FIGS. 1, 3, 4, 5, 6, and 7 (each contains the same framework regions and differ only in CDR sequences). These most preferred embodiments include the neutralizing antibody wherein the light chain variable region has the amino acid sequence of SEQ ID NO: 17 and the heavy chain variable region has the amino acid sequence of SEQ ID NO: 18; the neutralizing antibody wherein the light chain variable region has the amino acid sequence of SEQ ID NO: 19 and the heavy chain variable region has the amino acid sequence of SEQ ID NO: 20; the neutralizing antibody wherein the light chain variable region has the amino acid sequence of SEQ ID NO: 21 and the heavy chain variable region has the amino acid sequence of SEQ ID NO: 22; the neutralizing antibody wherein the light chain variable region has the amino acid sequence of SEQ ID NO: 23 and the heavy chain variable region has the amino acid sequence of SEQ ID NO: 24; the neutralizing antibody wherein the light chain variable region has the amino acid sequence of SEQ ID NO: 25 and the heavy chain variable region has the amino acid sequence of SEQ ID NO: 26.

It should be kept in mind that while the high affinity neutralizing antibodies of the present invention can be assembled from CDR regions and non-CDR regions derived from actual neutralizing antibodies by splicing amino acid segments together (and antibodies so assembled would be within the invention disclosed herein) the antibodies of the present invention are most conveniently prepared by genetically engineering appropriate gene sequences into vectors that may then be transfected into suitable cell lines for eventual expression of the assembled antibody molecules by the engineered cells. In fact, such recombinant procedures were employed to prepare the antibodies disclosed herein. In addition, because the sequences of the chains of the high affinity antibodies are known from the disclosure herein, such antibodies could also be assembled by direct synthesis of the appropriate chains and then allowed to self-assemble into tetrameric ($H_2L_2$) bivalent antibody structures.

The method of preparing the high affinity neutralizing antibodies of the invention involved the creation of a combinatorial library which was used to prepare clones producing antibodies comprising the beneficial CDRs of the invention that could then be screened for affinity for RSV epitopes (for Example, FIG. 2).

EXAMPLE 1

Kinetic Analysis of Humanized RSV Mabs by BIAcore™

The kinetics of interaction between high affinity anti-RSV Mabs and the RSV F protein was studied by surface plasmon resonance using a Pharmacia BIAcore™ biosensor. A recombinant baculovirus expressing a C-terminal truncated F protein provided an abundant source of antigen for kinetic studies. The supernatant, which contained the secreted F protein, was enriched approximately 20-fold by successive chromatography on concanavalin A and Q-sepharose columns. The pooled fractions were dialyzed against 10 mM sodium citrate (pH 5.5), and concentrated to approximately 0.1 mg/ml. In a typical experiment, an aliquot of the F-protein (100 ml) was amine-coupled to the BIAcore sensor chip. The amount immobilized gave approximately 2000 response units ($R_{max}$) of signal when saturated with the mouse monoclonal antibodies H1129 or H1308F (prepared as in U.S. Pat. No. 5,824,307, whose disclosure is hereby incorporated by reference). This indicated that there was an equal number of "A" and "C" antigenic sites on the F-protein preparation following the coupling procedure. Two unrelated irrelevant Mabs (RVFV 4D4 and CMV H758) showed no interaction with the immobilized F protein. A typical kinetic study involved the injection of 35 ml of Mab at varying concentrations (25-300 nM) in PBS buffer containing 0.05% Tween-20 (PBS/Tween). The flow rate was maintained at 5 ml/min, giving a 7 min binding phase. Following the injection of Mab, the flow was exchanged with PBS/Tween buffer for 30 min for determining the rate of dissociation. The sensor chip was regenerated between cycles with a 2 min pulse of 10 mM HCl. The regeneration step caused a minimal loss of binding capacity of the immobilized F-protein (4% loss per cycle). This small decrease did not change the calculated values of the rate constants for binding and dissociation (also called the $k_{on}$ and $k_{off}$ respectively).

More specifically, for measurement of $k_{assoc}$ (or $k_{on}$), F protein was directly immobilized by the EDC/NHS method (EDC=N-ethyl-N'-[3-diethylamino-propyl]carbodiimide; NHS=N-hydroxysuccinimide) with the F-protein being injected over the EDC/NHS activated sensor chip. Briefly, 4 µg/ml of F protein in 10 mM NaOAc, pH 4.0 was prepared and about a 30 µl injection gives about 500 RU (response units) of immobilized F protein under the above referenced conditions. The blank flow cell (VnR immobilized-CM dextran surface) was subtracted for kinetic analysis. The column could be regenerated using 100 mM HCl (with 72 seconds of contact time being required for full regeneration). This treatment removed bound Fab completely without damaging the immobilized antigen and could be used for over 40 regenerations. For $k_{on}$ measurements, Fab concentrations were 12.5 nM, 25 nM, 50 nM, 100 nM, 200 nM, and 400 nM. The dissociation phase was analyzed from 230 seconds (30 seconds after start of the dissociation phase) to 900 seconds. Kinetics were analyzed by 1:1 Langmuir fitting (global fitting). Measurements were done in HBS-EP buffer (10 mM HEPES, pH 7.4, 150 mM NaCl, 3 mM EDTA, 0.005% (v/v) Surfactant P20.

For measurements of combinatorial clones, as disclosed herein, the $k_{on}$ and $k_{off}$ were measured separately. The $k_{on}$ was measured at conditions that were the same as those for the single mutation clones and was analyzed similarly.

For measuring $k_{dissoc}$ (or $k_{off}$), the following conditions were employed. Briefly, 4100 RU of F protein were immobilized (as above) with CM-dextran used as the blank. Here, 3000 RU of Fab was bound (with dissociated Fab high enough to offset machine fluctuation). HBS plus 5 nM F protein (about 350-2000 times higher than the $K_{dissoc}$ or $K_d$—the dissociation equilibrium constant) was used as buffer. The dissociation phase was 6-15 hours at a flow rate of 5 μl/min. Under the conditions used herein, re-binding of the dissociated Fab was minimal. For further details, see the manual with the biosensor.

The binding of the high affinity anti-RSV antibodies to the F protein, or other epitopic sites on RSV, disclosed herein was calculated from the ratio of the first order rate constant for dissociation to the second order rate constant for binding or association ($K_d = k_{diss}/k_{assoc}$). The value for $k_{assoc}$ was calculated based on the following rate equation:

$$dR/dt = k_{assoc}[Mab]R_{max} - (k_{assoc}[Mab] + k_{diss})R$$

where R and $R_{max}$ are the response units at time t and infinity, respectively. A plot of dr/dt as a function of R gives a slope of ($k_{assoc}[Mab] + k_{diss}$)—Since these slopes are linearly related to the [Mab], the value $k_{assoc}$ can be derived from a replot of the slopes versus [Mab]. The slope of the new line is equal to $k_{assoc}$. Although the value of $k_{diss}$ can be extrapolated from the Y-intercept, a more accurate value was determined by direct measurement of $k_{diss}$. Following the injection phase of the Mab, PBS/Tween buffer flows across the sensor chip. From this point, [Mab]=0. The above stated equation for dR/dt thus reduces to:

$$dr/dt = k \text{ or } dR/R = k_{diss}dt$$

Integration of this equation then gives:

$$ln(R_0/R_t) = k_{diss}t$$

where $R_0/R_t$) are the response units at time 0 (start of dissociation phase) and t, respectively. Lastly, plotting $ln(R_0/R_t)$ as a function of t gives a slope of $k_{diss}$.

In the preferred embodiment herein, the numerical values from such antibody variants were as follows:

TABLE 4

Summary of Kinetic Constants from Ultra-high Affinity Antibodies.

| Clone ID | CDRs | $k_{assoc}$ (M$^{-1}$sec$^{-1}$) | $k_{diss}$ (sec$^{-1}$) | $K_a$ (M$^{-1}$) |
|---|---|---|---|---|
| 1 | AFSF | $1.13 \times 10^5$ | $1.62 \times 10^{-6}$ | $6.98 \times 10^{10}$ |
| 2 | AFFG | $1.33 \times 10^5$ | $1.82 \times 10^{-6}$ | $7.31 \times 10^{10}$ |
| 3 | PFFF | $1.10 \times 10^5$ | $1.35 \times 10^{-6}$ | $8.15 \times 10^{10}$ |
| 22 | AFFF | $1.34 \times 10^5$ | $3.70 \times 10^{-7}$ | $3.62 \times 10^{11}$ |
| 23 | AFFY | $1.22 \times 10^5$ | $3.03 \times 10^{-7}$ | $4.03 \times 10^{11}$ |

Here, the CDRs represent the amino acids replacing the reference amino acids at the key positions (or critical positions) of the CDRs shown in Table 1 (in bold and underlined) for a reference antibody. Thus, for example, clone 22 has an alanine at position 2 of CDR H1 (residue 32 of the heavy chain variable region—SEQ ID NO: 24) in place of the serine shown at that position in Table 1 (SEQ ID NO: 6), a phenylalanine at position 6 of CDR H3 (residue 105 of the heavy chain variable region—SEQ ID NO: 24) in place of the tryptophan shown at that position in Table 1 (SEQ ID NO: 8), a phenylalanine at position 3 of CDR L2 (residue 51 of the light chain variable region—SEQ ID NO: 23) in place of the serine shown at that position in Table 1 (SEQ ID NO: 4), and a phenylalanine at position 5 of CDR L3 (residue 92 of the light chain variable region —SEQ ID NO: 23) in place of the glycine shown at that position in Table 1 (SEQ ID NO: 5).

Of course, in forming such clones, Table 3 represents a pool of potential CDRs from which the high affinity CDRs of the antibodies of the present invention are to be drawn. For example, clone 23 of Table 4 uses the same CDRs as clone 22 with the exception of CDR L3, which has a tyrosine at position 5 of CDR L3 (Table 3—SEQ ID NO: 15) in place of the glycine shown in that position in Table 1 (SEQ ID NO: 5). The substitutions at the corresponding critical positions are likewise shown in Table 2.

EXAMPLE 2

Microneutralization Assay

Figure 8:
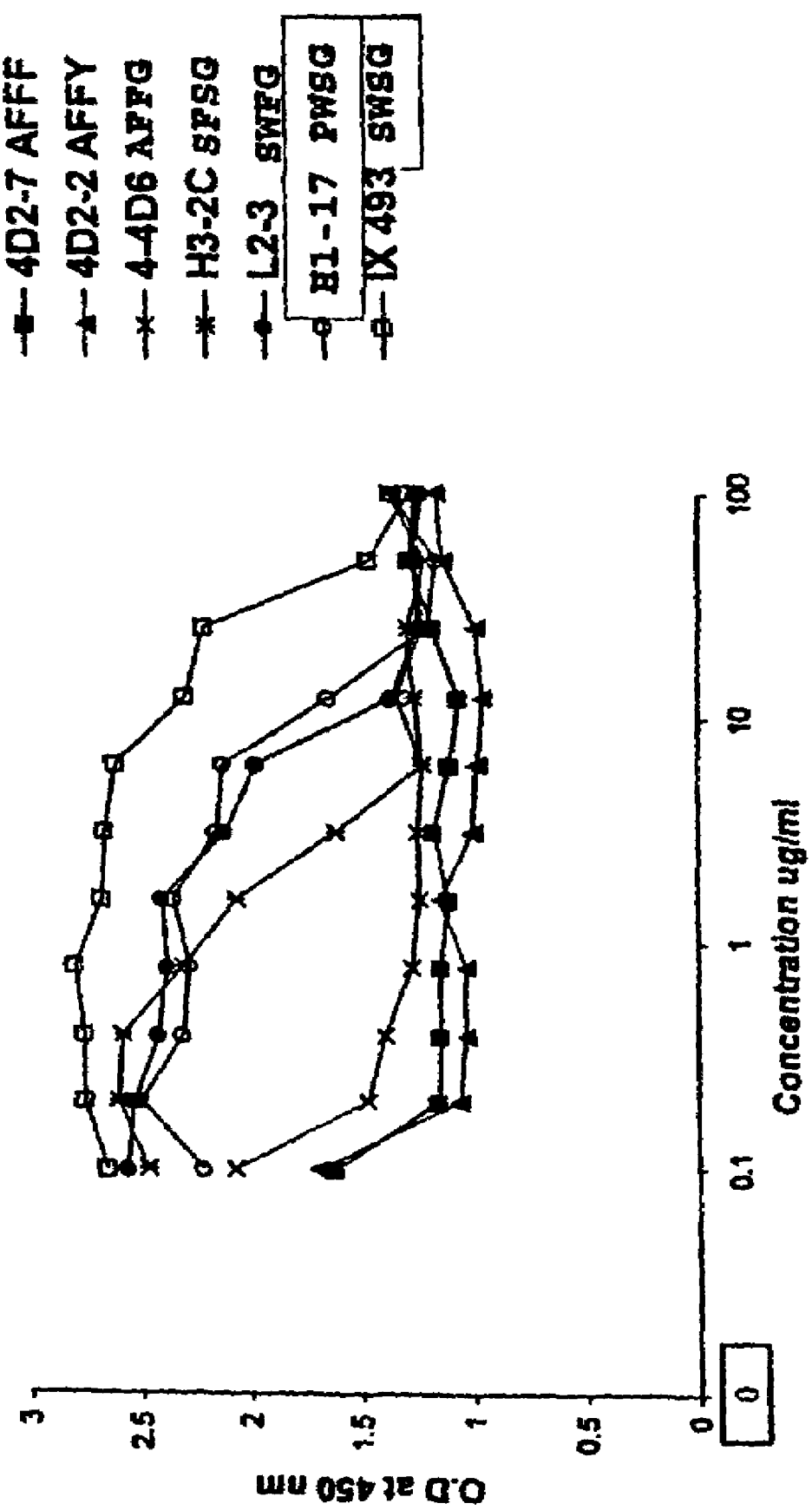
FIG. 8 shows the results of microneutralization experiments on several of the ultra-high affinity antibody clones disclosed herein. The amino acids present at the key positions of the high affinity complementarity determining regions (see Table 3) are shown at the right in the order H1, H3, L2, and L3 (as also shown in Table 2 where the clones are simply numbered but the table compares to this figure by relying on the actual amino acids used at the critical positions as disclosed in the Table and in the legend at the right of this figure). Thus, for clone 4D2-7, there is an alanine (A) at the key position of high affinity CDR H1, a phenylalanine (F) at the key position of high affinity CDR H3, a phenylalanine (F) at the key position of high affinity CDR L2, and a phenylalanine (F) at the key position of high affinity CDR L3. Briefly, about 25,000 HEp-2 cells were added to each of the wells of a 96 well plate along with RSV and a given concentration of the antibody (antibody concentration per well is shown on the abscissa— See Example 2 for exact details). After 5 days growth, the cells were fixed, treated with biotinylated anti-F MAb, then bound to avidin-peroxidase complex and the ability of the bound peroxidase to react thionitrobenzoic acid was determined by measuring O.D. at 450 nm. The amount of F protein present was an indicator of the extent of viral replication thereby resulting in more reaction of substrate by peroxidase and increased absorption. Thus, the lower the OD 450 value, the greater the neutralizing ability of the indicated concentration of the given antibody. Here, IX-493 (SWSG—meaning a serine (S) at the key position of high affinity CDR H1, a tryptophan (W) at the key position of high affinity CDR H3, a serine (S) at the key position of high affinity CDR L2, and a glycine (G) at the key position of high affinity CDR L3) is the "reference antibody" (also denoted L1 FR and IX-493L1 FR).
Figure 9:
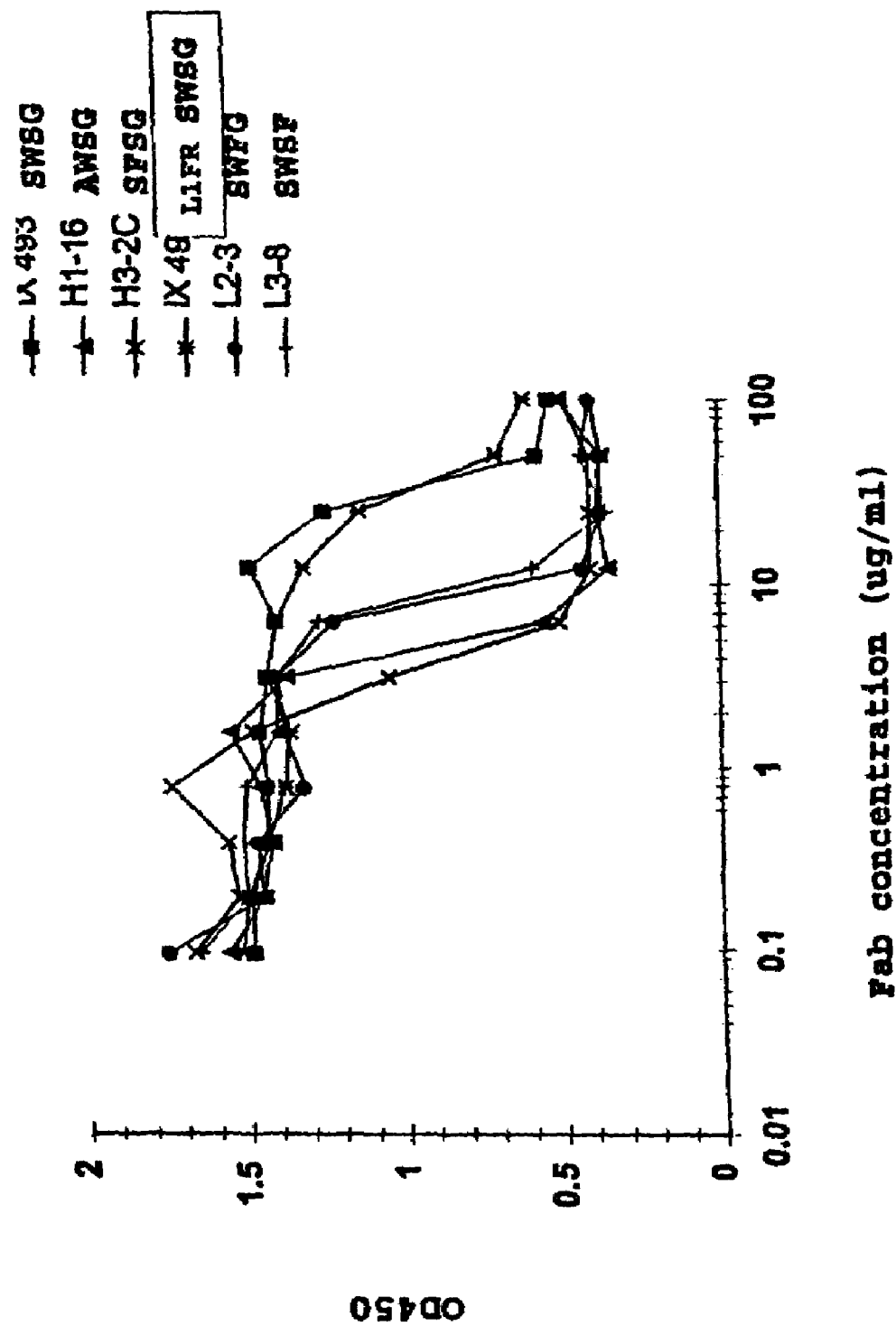
FIG. 9 shows results for microneutralization assays of several of the antibodies disclosed herein but where only Fab fragments were employed for neutralization of antibody replication. Here, IX-493 (SWSG) is the reference Fab fragment and is derived from antibody Medi-493 (see: Johnson et al (1997)—ref. 23).
Figure 10:
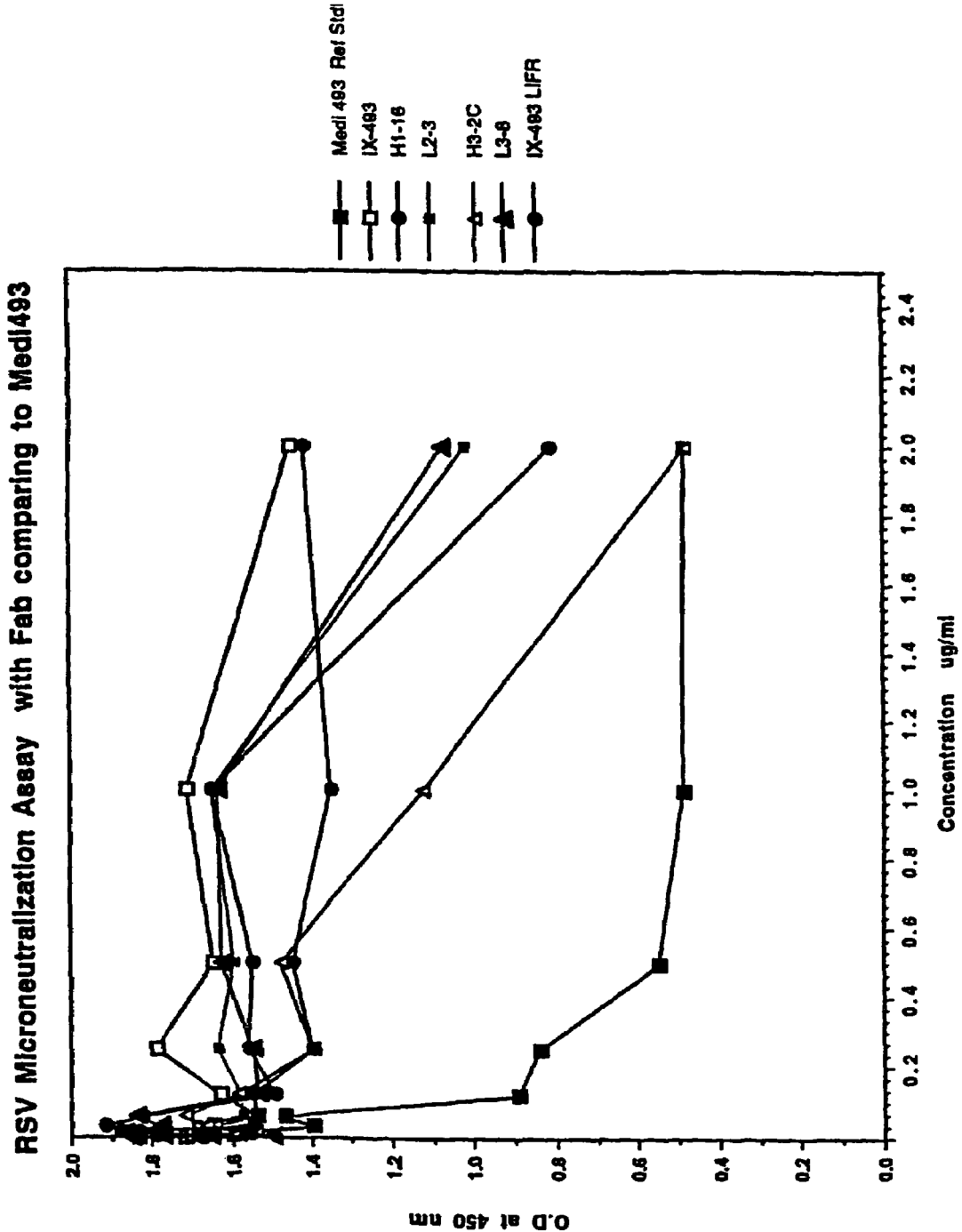
FIG. 10 shows the results of microneutralization for an antibody specific for RSV as compared to similar experiments for Fab fragments of the same antibody. Here, Medi 493 represents the antibody while IX-493 L1FR represents the Fab fragment of this antibody. The other lines are for Fab fragments of several of the antibodies produced according to the present invention (given various letter-digit code designations for internal identification but having nothing to do with their relative efficacy as neutralizing antibodies).

Neutralization of the antibodies of the present invention were determined by microneutralization assay. This microneutralization assay is a modification of the procedures described by Anderson et al (1985). Antibody dilutions were made in triplicate using a 96-well plate. Ten TCID$_{50}$ of respiratory syncytial virus (RSV—Long strain) were incubated with serial dilutions of the antibody (or Fabs) to be tested for 2 hours at 37° C. in the wells of a 96-well plate. RSV susceptible HEp-2 cells ($2.5 \times 10^4$) were then added to each well and cultured for 5 days at 37° C. in 5% CO$_2$. After 5 days, the medium was aspirated and cells were washed and fixed to the plates with 80% methanol and 20% PBS. RSV replication was then determined by F protein expression. Fixed cells were incubated with a biotin-conjugated anti-F protein monoclonal antibody (pan F protein, C-site-specific MAb 133-1H) washed and horseradish peroxidase conjugated avidin was added to the wells. The wells were washed again and turnover of substrate TMB (thionitrobenzoic acid) was measured at 450 nm. The neutralizing titer was expressed as the antibody concentration that caused at least 50% reduction in absorbency at 450 nm (the OD$_{450}$) from virus-only control cells. Results for several antibodies of the present invention are shown by the graph in FIG. 8 while results using Fab fragments are depicted in the graph of FIG. 9.

BACKGROUND AND CITED REFERENCES

1. Hall, C. B., Douglas, R. G., Geiman, J. M. et al., N. Engl. J. Med. 293:1343, 1975.
2. Hall, C. B., McBride, J. T., Walsh, E. E. et al., N. Engl. J. Med. 308:1443, 1983.
3. Hall, C. B., McBride, J. T., Gala, C. L. et al., JAMA 254:3047, 1985.
4. Wald, E. R., et al., J. Pediat. 112:154, 1988.
5. Kapikian, A. Z., Mithcell, R. H., Chanock, R. M. et al., Am. J. Epidemiol. 89:405, 1969.
6. Prince, G. A., Hemming, V. G., Horswood, R. L. et al., Virus Res. 3:193, 1985.
7. Hemming, V. G., Prince, G. A., Horswood, R. L. et al., J. Infect. Dis. 152:1083, 1985.
8. Wright, P. F., Belshe, R. B., et al., Infect. Immun. 37:397, 1982.
9. Conrad, D. A., Christenson, J. C., et al., Peditr. Infect. Dis. J. 6:152, 1987.
10. LoBuglio, A. F., Wheeler, R. L., Trang, J. et al., Proc. Natl. Acad. Sci. 86:4220, 1989.

11. Steplewski, Z., Sun, L. K., Shearman, C. W. et al., Proc. Natl. Acad. Sci. 85:4852, 1988.
12. Boulianne, G. L., Hozumi, N., Shulman, M. J. Nature. 312:643, 1984.
13. Sun, L. K., Curtis, P., Rakowicz-Szulczynska, E. et al., Proc. Natl. Acad. Sci. 84:214, 1987.
14. Liu, A. Y., Mack, P. W., Champion, C. I., Robinson, R. R., Gene 54:33, 1987.
15. Morrison, S. L., Johnson, M. J., Hersenber, L. A., Oi, V. T. Proc. Natl. Acad. Sci. 81:6851, 1984.
16. Morrison, S. L. Science 229:1202, 1985.
17. Sahagan, B. G., Dorai, H., Saltzgaber-Muller, J. et al., J. Immunol. 137:1066, 1986.
18. Taked, S., Naito, T., Hama, K., Noma, T., Honjo, T., Nature 314:452, 1985. 19. Carson, D. A., Freimark, B. D., Adv. Immunol. 38:275, 1986.
20. Beeler, J. A., et al., J. Virol. 63:2941-2950, 1989.
21. Coelingh, et al., Virology, 143:569-582,1985.
22. Anderson et al. Microneutralization test for respiratory syncytial virus based o an enzyme immunoassay, *J. Clin. Microbiol.* (1985) 22:1050-1052.
23. Johnson et al., Development of a humanized monoclonal antibody (MEDI-493) with potent in vitro and in vivo activity against respiratory syncytial virus, *J. Infectious Diseases* (1997) 176: 1215-1224.

What is claimed is:

1. A method for preventing a respiratory syncytial virus (RSV)-induced disease, comprising administering to a patient a high affinity neutralizing immunoglobulin that specifically binds to a RSV F antigen with an affinity constant ($K_a$) of at least $10^{10}$ M$^{-1}$ as measured by surface plasmon resonance, wherein the high affinity neutralizing immunoglobulin binds to the same epitope on the RSV F antigen as an antibody comprising a heavy chain variable region (VH) having an amino acid sequence SEQ ID NO:2 (FIG. 1B) and a light chain variable region (VL) having the amino acid sequence SEQ ID NO:1 (FIG. 1A).

2. A method for treating a respiratory syncytial virus-induced disease, comprising administering to a patient a high affinity neutralizing immunoglobulin that specifically binds to a RSV F antigen with a $K_a$ of at least $10^{10}$ M$^{-1}$ as measured by surface plasmon resonance, wherein the high affinity neutralizing immunoglobulin binds to the same epitope on the RSV F antigen as an antibody comprising a VH having the amino acid sequence SEQ ID NO:2 (FIG. 1B) and a VL having an amino acid sequence SEQ ID NO:1 (FIG. 1A).

3. The method of claims 1 or 2, wherein the immunoglobulin comprises one or more amino acid changes in one or more complementarity determining regions (CDRs) as compared to an existing antibody, wherein the existing antibody comprises:
   a. a VL comprising the following CDR sequences:
      VL CDR1 SASSSVGYMH (SEQ ID NO: 3),
      VL CDR2 DT[S]KLAS (SEQ ID NO: 4), and
      VL CDR3 FQGS[G]YPFT (SEQ ID NO 5); and
   b. a VH comprising the following CDR sequences:
      VH CDR1 T[S]GMSVG (SEQ ID NO: 6),
      VH CDR2 DIWWDDKKDYNPSLKS (SEQ ID NO: 7), and
      VH CDR3 SMITN[W]YFDV (SEQ ID NO: 8),
and wherein one or more amino acid residue substitutions are made at the boxed positions, such that the amino acid substitutions have the effect of producing an increase in the $K_a$ of the antibody.

4. The method of claims 1 or 2, wherein the immunoglobulin has a $K_a$ of at least $10^{11}$ M$^{-1}$.

5. The method of claim 3, wherein the immunoglobulin has a $K_a$ of at least $10^{11}$ M$^{-1}$.

6. The method of claim 1 or 2, wherein the immunoglobulin neutralizes RSV as measured by a microneutralization assay.

7. The method of claim 3, wherein the immunoglobulin neutralizes RSV as measured by a microneutralization assay.

8. The method of claim 4, wherein the immunoglobulin neutralizes RSV as measured by a microneutralization assay.

9. The method of claim 6, wherein the immunoglobulin has an IC$_{50}$ in the microneutralization assay that is less than the IC$_{50}$ of the IX-493 antibody.

10. The method of claim 7, wherein the immunoglobulin has an IC$_{50}$ in the microneutralization assay that is less than the IC$_{50}$ of the IX-493 antibody.

11. The method of claim 8, wherein the immunoglobulin has an IC$_{50}$ in the microneutralization assay that is less than the IC$_{50}$ of the IX-493 antibody.

12. The method of claim 1 or 2, wherein the immunoglobulin comprises:
   a. a VH CDR1 having the amino acid sequence TAGMSVG (SEQ ID NO:9);
   b. a VH CDR2 having the amino acid sequence DIWWDDKKDYNPSLKS (SEQ ID NO:7);
   c. a VH CDR3 having the amino acid sequence SMITNFYFDV (SEQ ID NO:11);
   d. a VL CDR1 having the amino acid sequence SASSSVGYMH (SEQ ID NO:3);
   e. a VL CDR2 having the amino acid sequence DTFKLAS (SEQ ID NO:12); and
   f. a VL CDR3 having the amino acid sequence FQGSFYPFT (SEQ ID NO: 14).

13. The method of claim 1 or 2, wherein the immunoglobulin is a tetrameric antibody, a Fab fragment, an F(ab)'$_2$, a heavy-light chain dimer, or a single chain structure.

14. The method of claim 1 or 2, wherein the immunoglobulin is a monoclonal antibody.

15. The method of claim 1 or 2, wherein the immunoglobulin is a humanized antibody.

16. The method of claim 12, wherein the immunoglobulin further comprises:
   (a) a framework region of a VL having the amino acid sequence of SEQ ID NO:1 and framework region of a VH having the amino acid of SEQ ID NO:2;
   (b) a framework region of a VL having the amino acid sequence of SEQ ID NO: 17 and framework region of a VH having the amino acid of SEQ ID NO:18;
   (c) a framework region of a VL having the amino acid sequence of SEQ ID NO: 19 and framework region of a VH having the amino acid of SEQ ID NO:20;
   (d) a framework region of a VL having the amino acid sequence of SEQ ID NO:21 and framework region of a VH having the amino acid of SEQ ID NO:22;
   (e) a framework region of a VL having the amino acid sequence of SEQ ID NO:23 and framework region of a VH having the amino acid of SEQ ID NO:24; or
   (f) a framework region of a VL having the amino acid sequence of SEQ ID NO:25 and framework region of a VH having the amino acid of SEQ ID NO:26.

17. The method of claim 1 or 2, wherein the immunoglobulin comprises a light chain variable region having the amino acid sequence of SEQ ID NO:23 and a heavy chain variable region having the amino acid sequence of SEQ ID NO:24.

18. The method of claim 1 or 2, wherein the patient is a human.

19. The method of claim 3, wherein the patient is a human.

20. The method of claim 4, wherein the patient is a human.

21. The method of claim 6, wherein the patient is a human.

22. The method of claim 8, wherein the patient is a human.

23. The method of claim 5, wherein the patient is a human.

24. The method of claim 7, wherein the patient is a human.

25. The method of claim 5, wherein the immunoglobulin neutralizes RSV as measured by a microneutralization assay.

26. The method of claim 25, wherein the patient is a human.

27. The method of claim 3, wherein the immunoglobulin is a monoclonal antibody.

28. The method of claim 3, wherein the immunoglobulin further comprises:
   (a) a framework region of a VL having the amino acid sequence of SEQ ID NO:1 and framework region of a VH having the amino acid of SEQ ID NO:2;
   (b) a framework region of a VL having the amino acid sequence of SEQ ID NO:17 and framework region of a VH having the amino acid of SEQ ID NO:18;
   (c) a framework region of a VL having the amino acid sequence of SEQ ID NO:19 and framework region of a VH having the amino acid of SEQ ID NO:20;
   (d) a framework region of a VL having the amino acid sequence of SEQ ID NO:21 and framework region of a VH having the amino acid of SEQ ID NO:22;
   (e) a framework region of a VL having the amino acid sequence of SEQ ID NO:23 and framework region of a VH having the amino acid of SEQ ID NO:24; or
   (f) a framework region of a VL having the amino acid sequence of SEQ ID NO:25 and framework region of a VH having the amino acid of SEQ ID NO:26.

29. The method of claim 1 or 2, wherein the Ka is $10^{10}$–$M^{-1}$.

30. The method of claim 3, wherein the Ka is $10^{10}$–$M^{-1}$.

31. The method of claim 1 or 2, wherein the Ka is $10^{11}$–$M^{-1}$.

32. The method of claim 3, wherein the Ka is $10^{11}$–$M^{-1}$.

* * * * *